United States Patent
McCurry et al.

(10) Patent No.: US 11,464,839 B2
(45) Date of Patent: Oct. 11, 2022

(54) METHODS AND VACCINES FOR INDUCING IMMUNE RESPONSES TO MULTIPLE DIFFERENT MHC MOLECULES

(71) Applicants: Mayo Foundation for Medical Education and Research, Rochester, MN (US); University of Washington, Seattle, WA (US)

(72) Inventors: Dustin B. McCurry, Phoenix, AZ (US); Peter A. Cohen, Scottsdale, AZ (US); Latha B. Pathangey, Scottsdale, AZ (US); Sandra J. Gendler, Scottsdale, AZ (US); Mary L. Disis, Renton, WA (US)

(73) Assignees: Mayo Foundation for Medical Education and Research, Rochester, MN (US); University of Washington, Seattle, WA (US)

( * ) Notice: Subject to any disclaimer, the term of this patent is extended or adjusted under 35 U.S.C. 154(b) by 778 days.

(21) Appl. No.: 15/781,393

(22) PCT Filed: Dec. 2, 2016

(86) PCT No.: PCT/US2016/064749
§ 371 (c)(1),
(2) Date: Jun. 4, 2018

(87) PCT Pub. No.: WO2017/096247
PCT Pub. Date: Jun. 8, 2017

(65) Prior Publication Data
US 2019/0000948 A1    Jan. 3, 2019

Related U.S. Application Data

(60) Provisional application No. 62/263,256, filed on Dec. 4, 2015.

(51) Int. Cl.
| | | |
|---|---|---|
| A61K 39/00 | (2006.01) | |
| A61K 39/245 | (2006.01) | |
| C07K 14/005 | (2006.01) | |
| A61K 39/12 | (2006.01) | |
| C07K 16/00 | (2006.01) | |
| A61P 35/02 | (2006.01) | |
| A61K 39/39 | (2006.01) | |

(52) U.S. Cl.
CPC ... *A61K 39/001114* (2018.08); *A61K 39/0011* (2013.01); *A61K 39/00117* (2018.08); *A61K 39/001106* (2018.08); *A61K 39/001168* (2018.08); *A61K 39/001184* (2018.08); *A61K 39/12* (2013.01); *A61K 39/245* (2013.01); *A61K 39/39* (2013.01); *A61P 35/02* (2018.01); *C07K 14/005* (2013.01); *C07K 16/00* (2013.01); *A61K 2039/55505* (2013.01); *A61K 2039/55511* (2013.01); *A61K 2039/55561* (2013.01); *A61K 2039/55566* (2013.01); *A61K 2039/55572* (2013.01); *C12N 2710/16122* (2013.01); *C12N 2710/16134* (2013.01)

(58) Field of Classification Search
CPC ........ A61K 39/0011; A61K 39/001168; A61K 39/001106; A61K 39/001184; A61K 39/00117; A61P 35/00; A61P 35/02; A61P 35/04
See application file for complete search history.

(56) References Cited

U.S. PATENT DOCUMENTS

| | | |
|---|---|---|
| 6,548,643 B1 | 4/2003 | McKenzie et al. |
| 6,734,172 B2 | 5/2004 | Scholler et al. |
| 7,202,346 B2 | 4/2007 | Payne et al. |
| 7,524,503 B2 | 4/2009 | Khanna et al. |
| 7,659,117 B2 | 2/2010 | Laus et al. |
| 7,820,786 B2 | 10/2010 | Thomson et al. |
| 7,935,804 B2 | 5/2011 | Dubensky, Jr. et al. |
| 8,815,249 B2 | 8/2014 | Humphreys et al. |
| 8,951,526 B2 | 2/2015 | Yonezawa |
| 2004/0101534 A1 | 5/2004 | Diamond |
| 2012/0308513 A1 | 12/2012 | Wollan et al. |
| 2013/0011424 A1 | 1/2013 | Maksyutov et al. |
| 2013/0011426 A1 | 1/2013 | Tureci et al. |
| 2013/0028915 A1 | 1/2013 | Palucka et al. |
| 2013/0108657 A1 | 5/2013 | Yee et al. |

(Continued)

FOREIGN PATENT DOCUMENTS

| | | |
|---|---|---|
| WO | WO 2001/074855 | 10/2001 |
| WO | WO 2001/082963 | 11/2001 |

(Continued)

OTHER PUBLICATIONS

Abstract of Rughetti et al. (Blood, 2008, vol. 112, p. 5237) (Year: 2008).*
Brinckerhoff et al. (International Journal of Cancer, 1999, vol. 83, pp. 326-334) (Year: 1999).*
Chhabra et al., The Scientific World Journal, 2011, vol. 11, pp. 121-129 (Year: 2011).*
European Search Report in European Application No. 16871630.6 dated Jul. 16, 2019, 16 pages.
European Search Report in European Application No. 16871630.6 dated Oct. 28, 2019, 10 pages.
Akiyama et al., "Identification of HLA-A24-restricted CTL epitope encoded by the matrix protein pp65 of human cytomegalovirus," Immunol. Lett., Aug. 2002, 83(1):21-30.

(Continued)

*Primary Examiner* — Karen A. Canella
(74) *Attorney, Agent, or Firm* — Fish & Richardson P.C.

(57) ABSTRACT

This document provides methods and materials relating to isolated polypeptides, polypeptide preparations, vaccine preparations (e.g., anti-cancer vaccine preparations), and methods for vaccinating mammals. For example, polypeptides (e.g., CMV, MUC1, HER2, Mesothelin (MESO), TRAG-3, or CALR polypeptides) having the ability to be processed into different polypeptides such that the processed polypeptides as a group are capable of being presented by different MHC molecules present in a particular mammalian population are provided.

16 Claims, 11 Drawing Sheets
Specification includes a Sequence Listing.

(56) References Cited

U.S. PATENT DOCUMENTS

| | | |
|---|---|---|
| 2013/0203163 A1 | 8/2013 | Wollan et al. |
| 2014/0286858 A1 | 9/2014 | Zimmerman et al. |
| 2015/0196628 A1 | 7/2015 | Mason et al. |

FOREIGN PATENT DOCUMENTS

| | | | |
|---|---|---|---|
| WO | WO 2005/049072 | 6/2005 | |
| WO | WO 2006/056027 | 6/2006 | |
| WO | 2009/059011 | 5/2009 | |
| WO | 2009/155535 | 12/2009 | |
| WO | WO 2011/110953 | 9/2011 | |
| WO | WO 2012/038055 | 3/2012 | |
| WO | WO-2013025972 A1 * | 2/2013 | ............... A61P 35/00 |
| WO | WO 2015/033140 | 3/2015 | |
| WO | 2015/100360 | 7/2015 | |
| WO | 2017/034833 | 3/2017 | |

OTHER PUBLICATIONS

Belyakov et al., "Mucosal immunization with HIV-1 peptide vaccine induces mucosal and systemic cytotoxic T lymphocytes and protective immunity in mice against intrarectal recombinant HIV-vaccinia challenge," Proc. Natl. Acad. Sci. U.S.A., Feb. 1998, 95(4):1709-1714.

Brinckerhoff et al., "Terminal modifications inhibit proteolytic degradation of an immunogenic MART-1(27-35) peptide: implications for peptide vaccines," Int. J. Cancer, Oct. 1999, 83(3):326-34.

Jackson et al., "A totally synthetic vaccine of generic structure that targets Toll-like receptor 2 on dendritic cells and promotes antibody or cytotoxic T cell responses" Proc. Natl. Acad. Sci. U.S.A., Oct. 2004, 101(43):15440-15445.

Karosiene et al., "NetMHCIIpan-3.0, a common pan-specific MHC class II prediction method including all three human MHC class II isotypes, HLA-DR, HLA-DP and HLA-DQ," Immunogenetics, Oct. 2013, 65(10):711-724.

Nielsen et al., "NetMHCIIpan-2.0—Improved pan-specific HLA-DR predictions using a novel concurrent alignment and weight optimization training procedure," Immunome Res., Nov. 2010, 6:9.

Wang et al., "CMVpp65 Vaccine Enhances the Antitumor Efficacy of Adoptively Transferred CD19-Redirected CMV-Specific T Cells," Clin. Cancer Res., Jul. 2015, 21(13):2993-3002.

Ackerman et al., "A role for the endoplasmic reticulum protein retrotranslocation machinery during crosspresentation by dendritic cells," Immunity, Oct. 2006, 25(4):607-617.

Ackerman et al., "Early phagosomes in dendritic cells form a cellular compartment sufficient for cross presentation of exogenous antigens," Proc. Natl. Acad. Sci. USA, Oct. 28, 2003, 100(22): 12889-12894.

Alves et al., "Differential regulation of human IL-7 receptor alpha expression by IL-7 and TCR signaling," J. Immunology, Apr. 15, 2008, 180(8):5201-5210.

Apostolopoulos et al., "A glycopeptide in complex with MHC class I uses the GalNAc residue as an anchor," Proc. Natl. Acad. Sci. USA, Dec. 1, 2003, 100(25): 15029-15034.

Arentz-Hansen et al., "Celiac lesion T cells recognize epitopes that cluster in regions of gliadins rich in proline residues," Gastroenterology, Sep. 2002, 123(3):803-809.

Belizaire et al., "Targeting proteins to distinct subcellular compartments reveals unique requirements for MHC class I and II presentation," Proc. Natl. Acad. Sci. USA, Oct. 13, 2009, 106(41):17463-17468.

Caserta et al., "IL-7 is superior to IL-2 for ex vivo expansion of tumour-specific CD4(+) T cells," Eur. J. Immunology, Feb. 2010, 40(2):470-479.

Cieri et al., "IL-7 and IL-15 instruct the generation of human memory stem T cells from naive precursors," Blood, Jan. 24, 2013, 121(4):573-584.

Cohen et al., "CD4+ T cells in adoptive immunotherapy and the indirect mechanism of tumor rejection," Crit. Rev. Immunology, 2000, 20(1):17-56.

Cohen et al., "STAT3- and STAT5-dependent pathways competitively regulate the pan-differentiation of CD34pos cells into tumor-competent dendritic cells," Blood, Sep. 1, 2008, 112(5):1832-1843.

Cohen et al., "T-cell adoptive therapy of tumors: Mechanisms of improved therapeutic performance," Crit. Rev. Immunology, 2001, 21(l-3):215-248.

Crespo et al., "TLR7 triggering with polyuridylic acid promotes cross-presentation in CD8alpha+ conventional dendritic cells by enhancing antigen preservation and MHC class I antigen permanence on the dendritic cell surface," J. Immunology, Feb. 2013, 190(3):948-960.

Delamarre et al., "Presentation of exogenous antigens on major histocompatibility complex (MHC) class I and MHC class II molecules is differentially regulated during dendritic cell maturation," J. Exp. Medicine, Jul. 7, 2003, 198(1):111-122.

Deshpande et al., "IL-7- and IL-15-mediated TCR sensitization enables T cell responses to self-antigens," J. Immunology, Feb. 15, 2013, 190(4): 1416-1423.

Di Genova et al., "Bystander stimulation of activated CD4+ T cells of unrelated specificity following a booster vaccination with tetanus toxoid," Eur. J. Immunology, Apr. 2010, 40(4):976-985.

Disis et al., "Concurrent Trastuzumab and HER2/neu-Specific Vaccination in Patients With Metastatic Breast Cancer," J. Clin. Oncology, 27(28): 4685-4692.

Disis et al., "Generation of T-cell immunity to the HER-2/neu protein after active immunization with HER-2/neu peptide-based vaccines," J. Clin. Oncology, Jun. 1, 2002, 20(11):2624-2632.

Disis et al., "HER-2/neu vaccine-primed autologous T-cell infusions for the treatment of advanced stage HER-2/neu expressing cancers," Cancer Immunol. Immunotherapy, Feb. 2014, 63(2): 101-109.

Dudley et al., "Adoptive cell transfer therapy following non-myeloablative but lymphodepleting chemotherapy for the treatment of patients with refractory metastatic melanoma," J. Clin. Oncology, Apr. 1, 2005, 23(10):2346-2357.

Dudley et al., "Cancer regression and autoimmunity in patients after clonal repopulation with antitumor lymphocytes," Science, Oct. 25, 2002, 298(5594):850-854.

Dudley et al., "Randomized selection design trial evaluating CD8+-enriched versus unselected tumor-infiltrating lymphocytes for adoptive cell therapy for patients with melanoma," J. Clin. Oncology, Jun. 10, 2013,31(17):2152-2159.

Faure et al., "Long-lasting cross-presentation of tumor antigen in human DC," Eur. J. Immunology, Feb. 2009, 39(2)380-390.

Fraser et al., "Generation of a universal CD4 memory T cell recall peptide effective in humans, mice and non-human primates," Vaccine, May 19, 2014, 32(24):2896-2903.

Gagnon et al., "Increased antigen responsiveness of naive CD8 T cells exposed to IL-7 and IL-21 is associated with decreased CD5 expression," Immunol, Cell Biology, May-Jun. 2010, 88(4):451-460.

Garulli et al., "Primary CD8+ T-cell response to soluble ovalbumin is improved by chloroquine treatment in vivo," Clin. Vaccine Immunology, Oct. 2008, 15(10):1497-1504.

Gragert et al., "Six-locus high resolution HLA haplotype frequencies derived from mixed-resolution DNA typing for the entire US donor registry," Hum. Immunology, Oct. 2013, 74(10):1313-1320.

Hattrup et al., "Structure and function of the cell surface (tethered) mucins," Annu. Rev. Physiology, 2008, 70:431-457.

Hertz et al., "HIV-1 Vaccine-Induced T-Cell Reponses Cluster in Epitope Hotspots that Differ from Those Induced in Natural Infection with HIV-1," PLoS Pathogens, Jun. 20, 2013, 9(6):el003404, 14 pages.

Heukamp et al., "Identification of three non-VNTR MUCl-derived HLA-A*0201-restricted T-cell epitopes that induce protective antitumor immunity in HLA-A2/K(b)-transgenic mice," Int. J. Cancer, Feb. 2001, 91(3)385-392.

Imai et al., "Exogenous antigens are processed through the endoplasmic reticulum-associated degradation (ERAD) in cross-presentation by dendritic cells," Int. Immunology, Jan. 2005, 17(l):45-53.

Kaech et al., "Selective expression of the interleukin 7 receptor identifies effector CD8 T cells that give rise to long-lived memory cells," Nat. Immunology, Dec. 2003,4(12): 1191-1198.

(56) References Cited

OTHER PUBLICATIONS

Kaiyampudi et al., "A degenerate HLA-DR epitope pool of HER-2/neu reveals a novel in vivo immunodominant epitope, HER-2/neu88-102," Clin. Cancer Research, Feb. 1, 2010, 16(3):825-834.
Katz et al., "T cell receptor stimulation impairs IL-7 receptor signaling by inducing expression of the microRNA miR-17 to target Janus kinase 1," Sci. Signaling, Aug. 26, 2014, 7(340):ra83, 10 pages.
Kisselev et al., "Proteasome inhibitors: from research tools to drug candidates," Chem. Biology, Aug. 2001, 8(8):739-758.
Knutson et al., "IL-12 enhances the generation of tumour antigen-specific Th1 CD4 T cells during ex vivo expansion," Clin. Exp. Immunology, Feb. 2004, 135(2)322-329.
Knutson et al., "Immunization with a HER-2/neu helper peptide vaccine generates HER-2/neu CD8 T-cell immunity in cancer patients," J. Clin. Investigation, Feb. 2001, 107(4):477-484.
Kobayashi et al., "Defining promiscuous MHC class II helper T-cell epitopes for the HER2/neu tumor antigen," Cancer Research, Sep. 15, 2000, 60(18):5228-5236.
Koenen et al., "Mutually exclusive regulation of T cell survival by IL-7R and antigen receptor-induced signals," Nat. Communications, Apr. 16, 2013, 4:1735, 10 pages.
Kovjazin et al., "ImMucin: a novel therapeutic vaccine with promiscuous MHC binding for the treatment of MUC1-expressing tumors," Vaccine, Jun. 24, 2011, 29(29-30):4676-4686.
Kreer et al., "Cross-presentation: how to get there—or how to get the Erm" Front. Immunology, Jan. 3, 2012, 2:87, 10 pages.
Kruit et al., "Selection of immunostimulant AS15 for active immunization with MAGE-A3 protein: results of a randomized phase II study of the European Organisation for Research and Treatment of Cancer Melanoma Group in Metastatic Melanoma," J. Clin. Oncology, Jul. 1, 2013, 31(19):2413-2420.
Lu et al., "Efficient identification of mutated cancer antigens recognized by T cells associated with durable tumor regressions," Clin. Cancer Research, Jul. 1, 2014, 20(13):3401-3410.
Madan et al., "Clinical evaluation of TRICOM vector therapeutic cancer vaccines," Semin. Oncology, Jun. 2012, 39(3):296-304.
Markley et al., "IL-7 and IL-21 are superior to IL-2 and IL-15 in promoting human T cell-mediated rejection of systemic lymphoma in immunodeficient mice," Blood, Apr. 29, 2010, 115(17):3508-3519.
McKinstry et al., "Effector CD4 T-cell transition to memory requires late cognate interactions that induce autocrine IL-2," Nat. Communications, Nov. 5, 2014, 5:5377, 12 pages.
Melief et al., "Immunotherapy of established (pre)malignant disease by synthetic long peptide vaccines," Nat. Rev. Cancer, May 2008, 8(5):351-360.
Men et al., "MHC class I- and class II-restricted processing and presentation of microencapsulated antigens," Vaccine, Mar. 5, 1999, 17(9-10): 1047-1056.
Ménager et al., "Cross-presentation of synthetic long peptides by human dendritic cells: a process dependent on ERAD component p97/VCP but Not sec61 and/or Derlin-1," PLoS One, Feb. 27, 2014, 9(2):e89897, 13 pages.
Morgan et al., "High efficiency TCR gene transfer into primary human lymphocytes affords avid recognition of melanoma tumor antigen glycoprotein 100 and does not alter the recognition of autologous melanoma antigens," J. Immunology, Sep. 15, 2003, 171(6):3287-3295.
PCT International Preliminary Report on Patentability in International Appln. No. PCT/US2016/064749, dated Jun. 5, 2018, 8 pages.

PCT International Search Report and Written Opinion in International Appln. No. PCT/US2016/064749, dated Apr. 28, 2017, 13 pages.
Peng et al., "Helper-independent, L-selectin(low) CD8(+) T cells with broad anti-tumor efficacy are naturally sensitized during tumor progression," J. Immunology, Nov. 15, 2000, 165(10):5738-5749.
Quoix et al., "Therapeutic vaccination with TG4010 and first-line chemotherapy in advanced non-small-cell lung cancer: a controlled phase 2B trial," Lancet Oncology, Nov. 2011, 12(12):1125-1133.
Rongcun et al., "Identification of new HER2/neu-derived peptide epitopes that can elicit specific CTL against autologous and allogeneic carcinomas and melanomas," J. Immunology, Jul. 15, 1999, 163(2):1037-1044.
Rosalia et al., "Dendritic cells process synthetic long peptides better than whole protein, improving antigen presentation and T-cell activation," Eur. J. Immunology, Oct. 2013, 43(10):2554-2565.
Sabbatini et al., "Phase I trial of overlapping long peptides from a tumor self-antigen and poly-ICLC shows rapid induction of integrated immune response in ovarian cancer patients," Clin. Cancer Research, Dec. 1, 2012, 18(23):6497-6508.
Salazar et al., "Persistent immunity and survival after immunization with a HER2/neu (HER2) vaccine," J. Clin. Oncology, May 20, 2009, 27(15 suppl):3010, 4 pages.
Sinnathamby et al., "Presentation by recycling MHC class II molecules of an influenza hemagglutinin-derived epitope that is revealed in the early endosome by acidification," J. Immunology, Apr. 1, 2003, 170(7):3504-3513.
Slingluff Jr. et al., "A randomized phase II trial of multiepitope vaccination with melanoma peptides for cytotoxic T cells and helper T cells for patients with metastatic melanoma (E1602)," Clin. Cancer Research, Aug. 1, 2013, 19(15):4228-4238.
Slingluff Jr. et al., "Immunologic and clinical outcomes of a randomized phase II trial of two multipeptide vaccines for melanoma in the adjuvant setting," Clin. Cancer Research, Nov. 1, 2007, 13(21):6386-6395.
Surman et al., "Localization of CD41 T cell epitope hotspots to exposed strands of HIV envelope glycoprotein suggests structural influences on antigen processing," Proc. Natl. Acad. Sci. USA, Apr. 10, 2011, 98(8):4587-4592.
Tewari et al., "A cytosolic pathway for MHC class II-restricted antigen processing that is proteasome and TAP dependent," Nat. Immunology, Mar. 2005, 6(3):287-294.
Tran et al., "Cancer immunotherapy based on mutation-specific CD4+ T cells in a patient with epithelial cancer," Science, May 9, 2014, 344(6184):641-645.
Wang et al., "Adoptive transfer of tumor-primed, in vitro-activated, CD4(+) T effector cells (T(E)s) combined with CD8(+) T(E)s provides intratumoral T-E proliferation and synergistic antitumor response," Blood, Jun. 1, 2007, 109(11):4865-4872.
Zehner et al., "The translocon protein sec61 mediates antigen transport from endosomes in the cytosol for cross-presentation to CD8(+) T cells," Immunity, May 19, 2015, 42(5):850-863.
Zeng et al., "Synergy of IL-21 and IL-15 in regulating CD8+ T cell expansion and function," J. Exp. Medicine, Jan. 3, 2005, 201(1):139-148.
Zhang et al., "Comparing pooled peptides with intact protein for accessing cross-presentation pathways for protective CD8+ and CD4+ T cells," J. Biol. Chemistry, Apr. 3, 2009, 284(14):9184-9191.
Zhang et al., "Hotspot Hunter: a computational system for large-scale screening and selection of candidate immunological hotspots in pathogen proteomes," BMC Bioinformatics, 2008, 9(Suppl 1):S19, 9 pages.

* cited by examiner

```
  1 mtpgtqspff lllllltvltv vtgsghasst pggeketsat qrssvpsste knavsmtssv
 61 lsshspgsgs sttqgqdvtl apatepasgs aatwgqdvts vpvtrpalgs ttppahdvts
121 apdnkpapgs tappahqvts apdtrpapgs tappahqvts apdtrpapgs tappahqvts
181 apdtrpapgs tappahqvts apdtrpapgs tappahqvts apdtrpapgs tappahqvts
241 apdtrpapgs tappahqvts apdtrpapgs tappahqvts apdtrpapgs tappahqvts
301 """""""""" """""""""" """""""""" """""""""" """""""""" """"""""""
361 """""""""" """""""""" """""""""" """""""""" """""""""" """"""""""
421 """""""""" """""""""" """""""""" """""""""" """""""""" """"""""""
481 """""""""" """""""""" """""""""" """""""""" """""""""" """"""""""
541 """""""""" """""""""" """""""""" """""""""" """""""""" """"""""""
661 """""""""" """""""""" """""""""" """""""""" """""""""" """"""""""
721 """""""""" """""""""" """""""""" """""""""" """""""""" """"""""""
781 """""""""" """""""""" """""""""" """""""""" """""""""" """"""""""
841 """""""""" """""""""" """""""""" """""""""" """""""""" """"""""""
901 apdtrpapgs tappahqvts apdtrpapgs tappahqvts apdnrpalgs tappvhnvts
961 asgsasgsas tlvhngtsar atttpaskst pfsipshhsd tpttlashst ktdassthhs
1021 svppltssnh stspqlstgv sffflsfhis nlqfnssled pstdyyqelq rdisemflqi
```

FIG. 1

```
1081 ykqggflgls nikfrpgsvv vqltlafreg tinvhdvetq fnqykteaas rynltisdvs
                                                              *=======>
           =======18±6+    ==============19±8+                =======>
             ==============22±4+            ==================20±6 +
1141 vsdvpfpfsa qsgagvpgwg iallvlvcvl valaivylia lavcqcrrkn ygqldifpar
     =/23++                *==========24 ++ *
       ======16±4 + *      *==========29/++*
                            *==========24/++*
                              *==========28/++*
                                *==========24/++*
                                  *==========24/++*
                              ================18±5 ++*
                              ================18±4 ++*
                            ================18±5 ++*
                                ================16±5 ++*
                                  ================17±4 ++*
                                    ================20±7 ++*
                                      ================19±5 ++*
                                        ================17±5 ++*
                                          ================19±4 ++*
                                            ================19±4 ++*
                                              ================20±8 ++*
1201 dtyhpmseyp tyhthgryvp psstdrspye kvsagnggss lsytnpavaa asanl
                                       *==========23/++*
                                         ================16±4++*
```

FIG. 1 (Cont.)

MUC1

```
  1  M T PGTQSPF FLLLLTVL T V V T G S H A S S T P G G E K
 36  E T S A T Q R S S V P S STEKNAVSMT S S V L S S H S P G S G S
 71  S T T Q G Q D V T L A P A T E P A S G S A A T WGQDVT S V P V TR
106  P A L G S T T P P A H D V T S A P D N K P A P G S T A P P AHGVTS
141  APDTRPAPGSTAPPAHGVT S A P D N R P A L G S TAPPV
176  H N V T S A S G S A SGSASTL V H N G T S A R A T T T P A S K S T
211  P F S I P S H H S D T P T T L A S H S T K T D A S S T H H S S V P P L
246  T S S NHSTSPQLSTGVSFFFLS F H I S N L Q F N S S L E D
281  P S T D Y Y Q E L Q R D I S E M F L Q I Y K Q G G F L G L S N I K F R
316  PGSVVVQLT L A F R E G T I N V H D VETQFNQ Y K TEAAS
351  RY N L T I S D V S V S D V P F P F S A Q S G A G V P G W G I A L L V
386  LVCVLVALAIVYLIALAV C QCRRKNYGQ L D I F P A R
421  D T Y H PMSEY P T Y H T H G R Y V P P S S T D R S P Y E K V S A G
456  NGGSSL S Y T N P A V A A T S A N L
```

FIG. 2A

HER2/neu

```
   1  MELAALCHWGLL LALLPPGAA STQVCTGTDM KLHL PASPETHLDML HHLYOGCQ VVQGNLELTY LPTNAS LSFLQD IQEV
  81  QGYVLIAHNQVRQVPLQRL RIV RGTQL FEDNYALAVLDNGDPLNNTTPVT GASPGGLRELQLRSLTEILKGGV LIQRNPQ
 161  LCYQDTILWKDIF HKNNQL ALTLIDTNRSRACHPCSPMCKGSRCWGESSEDCQSLTRTVCAGGCARCKGPLPTDCCHEQC
 241  AAGCTGP KHSDCLA CLHF NHSGI CELHCPALVTYNTDTFESMPNPEGRY TEGASCVTACPY NYLST DVGSC TLVCPLHNQ
 321  EVTAEDGTQRCEKCS KPCARVCYGLGMCHLAEV RAV ISANIQEFAGGKKI FGSLAFLPESFDGDPASNTAPLQPEQ LQVF
 401  ETLEELTGY LYISAWPD SLPDLSVFQNLQVIRGRI LH NGAYSLILQGLGISWLGLRSLRELGSGLAL I H HNTHL CFVH TV
 481  PWDQLFRNPHQA LLHTANRPEDEC VGEGLA CHQLCARGHCW GRGPTQ CVNCSQFLRG QECVEECRVLQGLPR EYVNARHC
 561  LPCHPECQPQNGSVTCFGPEADQCVACAHY KDPE FCVARCP SGVKPDL SYMPIWKFPDEEGACQPCPINCTHSCVDLDDK
 641  GCPA EQRASPLT SIISAVVGILL VVVLGVVFGILI IXRRQKIRKYT MRALLQETELVEPLT PSGAMPNQAQMRILKETEL
 721  RKV KVLGSGAFGTVYKGIW IPDGENVKIPVAI KVLRENTSPKANKEI LDEAY VMA GVGSPYVSRLLGICLTSTV QLVTQL
 801  MPYGCLL DHVRENRGR LGSQDLLNWCMQ IAKGMSYLEDVRLVHRDLAARNVLVK SPNHVKIT DFGLARLLDIDETEYHAD
 861  GGKVPIKWMALESILR RRFTHQSDVWSY GVTVWEL MTFGAKPYDGIPAREIPDLLEKGERL PQPPICTIDVY MIMVKCWM
 961  ID SECRPRERELVSEFSR MARDPQR VVIQNEDLGPASPLDSTFYRSLLEDDDMGDLVDAEEYLVPQQGFFCPDP APGAG
1041  GM VHHRHRSSSTRSGGGDLTLGLEPSEEEAPASPLAPSEGAGSDVFDGDLGMAAKGLQSLPTHDPSPLQRYSEDPTVPL
1121  PSETDGYVAPLTCSPQPEYVNQPDVRPQPPSPREGPLPAARPAGATLERPKTLSPGKNGVVKDVFAFGGAVENPEYLTPQ
1201  GGAAPQPHPPPAFSPAFDNLYYWDQDPPERGAPPSTFKGTPTAENPEYLGLDVPV
```

FIG. 2B

Modified CALR C-terminus

R R M M R T K M R M R R M R R T R R K M S P A R P R T S C R E A C L Q G W T E A

METHODS AND VACCINES FOR INDUCING IMMUNE RESPONSES TO MULTIPLE DIFFERENT MHC MOLECULES

CROSS-REFERENCE TO RELATED APPLICATIONS

This application is a National Stage application under 35 U.S.C. § 371 of International Application No. PCT/US2016/064749, having an International Filing Date of Dec. 2, 2016, which claims the benefit of priority to U.S. Provisional Application Ser. No. 62/263,256, filed Dec. 4, 2015. The disclosures of the prior applications are considered part of (and are incorporated by reference in) the disclosure of this application.

SEQUENCE LISTING

The instant application contains a Sequence Listing which has been submitted electronically in ASCII format and is hereby incorporated by reference in its entirety. Said ASCII copy, created on Dec. 16, 2021, is named 07039-1505US1_ST25.txt and is 45 KB bytes in size.

STATEMENT AS TO FEDERALLY SPONSORED RESEARCH

This invention was made with government support under CA136632 and CA102701 awarded by the National Institutes of Health. The federal government has certain rights in the invention.

BACKGROUND

1. Technical Field

This document provides methods and materials relating to isolated polypeptides, polypeptide preparations, vaccine preparations (e.g., anti-cancer vaccine preparations), and methods for vaccinating mammals. For example, this document provides polypeptides having the ability to be processed into a collection of different polypeptides such that the polypeptides of the collection are capable of being presented by different major histocompatibility complex (MHC) molecules present in a particular mammalian population.

2. Background Information

Polypeptide-based vaccines use polypeptide sequences derived from target proteins as epitopes to provoke an immune reaction. These vaccines are a result of an improved understanding of the molecular basis of epitope recognition, thereby permitting the development of rationally designed, epitope-specific vaccines based on motifs demonstrated to bind to MHC molecules.

SUMMARY

This document provides methods and materials relating to isolated polypeptides, polypeptide preparations, vaccine preparations (e.g., anti-cancer vaccine preparations), and methods for vaccinating mammals. For example, this document provides polypeptides (e.g., CMV pp65, MUC1, HER2, Mesothelin (MESO), TRAG-3, or Calreticulin (CALR) polypeptides) having the ability to be processed into different polypeptides such that the processed polypeptides as a group are capable of being presented by different MHC molecules present in a particular mammalian population. In some cases, the group of processed polypeptides can bind to at least 85 percent (e.g., at least about 87, 90, of 95 percent) of the MHC molecules present in a particular mammalian population such as humans.

This document also provides methods and materials (e.g., vaccine preparations) for treating cancer. For example, the vaccine preparations provided herein can include one or more of the MUC1, HER2, MESO, TRAG-3, or CALR polypeptides provided herein (see, e.g., Table 1) and can have the ability to induce a protective or therapeutic immune response within a mammal (e.g., a human).

As described herein, polypeptides ranging from about 18 to about 55 (e.g., about 18 to about 50, about 20 to about 50, about 25 to about 50, about 30 to about 50, about 18 to about 45, about 18 to about 40, about 18 to about 35, about 20 to about 45, about 25 to about 40, or about 30 to about 35) amino acid residues in length were identified, produced, and confirmed to have the ability to induce immune responses in the context of multiple different MHC molecules. The identification of these polypeptides can be used to aid in understanding immune processes and can be used to generate anti-cancer vaccine preparations.

In general, one aspect of this document features an isolated polypeptide, wherein the amino acid sequence of the polypeptide is as set forth in any one of SEQ ID NOs:1-58.

In another aspect, this document features a composition comprising, or consisting essentially of, at least one isolated polypeptide selected from the group consisting of SEQ ID NOs:1-58. The composition can further comprise an adjuvant.

In another aspect, this document features a method of treating cancer or a precancerous condition in a mammal. The method comprises, or consists essentially of, administering to the mammal a composition comprising an adjuvant and at least one polypeptide, wherein the amino acid sequence of the polypeptide is as set forth in any one of SEQ ID NOs:1-58. The mammal can be a human. The cancer can be breast cancer, pancreatic cancer, ovarian cancer, stomach cancer, lung cancer, colon cancer, multiple myeloma, leukemia, brain cancer, or melanoma cancer. The precancerous condition can be primary myelofibrosis, essential thrombocythemia or polycythemia vera. The adjuvant can be CpG, aluminum sulfate, aluminum phosphate, MF59, Pam3CSK4, LPS, polyIC, imiquimod, or R848.

In another aspect, this document features a vaccine comprising an adjuvant and at least one polypeptide, wherein the amino acid sequence of the polypeptide is as set forth in any one of SEQ ID NOs:1-58. The adjuvant can be CpG, aluminum sulfate, aluminum phosphate, MF59, Pam3CSK4, LPS, polyIC, imiquimod, or R848.

In another aspect, this document features a method of inducing an immune response against at least one polypeptide, wherein the sequence of the polypeptide is as set forth in any one of SEQ ID NOs:1-58, wherein the method comprises administering the polypeptide to a mammal in an amount effective to induce an immune response against the polypeptide. The polypeptide can be administered in combination with an adjuvant. The adjuvant can be CpG, aluminum sulfate, aluminum phosphate, MF59, Pam3CSK4, LPS, polyIC, imiquimod, or R848.

In another aspect, this document features a method of identifying a polypeptide between 18 and 50 amino acids in length, wherein the polypeptide includes epitopes that bind to at least 20 different HLA-DR types, wherein the method comprises determining the binding affinity of epitopes within the polypeptide for the at least 20 different HLA-DR types. The at least 20 different HLA-DR types can be selected by identifying (a) HLA-DRB1 alleles with greater than 6% frequency in 1 or more population groups, (b) HLA-DRB1 alleles with greater than 3% frequency in 2 or more population groups, (c) HLA-DRB1 alleles with greater than 1.5% frequency in 3 or more population groups, and (d) for population groups with less than 89.0% coverage, adding the next highest allele frequencies for that group, until 89% coverage.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 illustrates promising MHC binding peptide epitopes identified using the program "SYFPEITHI." The illustration analyzes the full the amino acid sequence for the protein MUC1 (SEQ ID NO:76). The part of the sequence located inside the box represents the variable number of tandem repeats domain (VNTR). Each sequence underlined and labeled with "#" is predicted to bind to the limited number (six) of HLA-DR molecules that are included in the SYFPEITHI algorithm. Each sequence underlined and labeled with "##" is predicted to bind to HLA-A2, as predicted by the SYFPEITHI algorithm. Areas labeled with "^" have both HLA-DR and HLA-A2 predicted epitopes. The numbers beside represent SYFPEITHI arbitrary binding scores+/− standard deviation for the HLA-DR types tested by SYFPEITHI. This type of analysis has been employed to synthesize peptides 15-17 amino acids long which can directly bind to HLA-DRB1 (MHC Class II) molecules, as well as peptides 8-9 amino acids long which can directly bind to HLA-A2 (MHC Class I) molecules.

FIGS. 2A-2C are results from an antigen discovery algorithm. FIG. 2A is the amino acid sequence for a MUC1 polypeptide (SEQ ID NO:77). Each amino acid is shaded based upon the frequency of HLA-DRB1 (MHC Class II) molecules that epitope is predicted to bind. Epitopes begin with the shaded-coded amino acid and are 15 amino acids long. "Dead" epitopes are light in shade and range to darker for epitopes with a high frequency of binding. This allows for a graphical "heat map" of the immunogenic regions within polypeptides and graphically represents the advancement over other techniques for the polypeptides described herein. FIG. 2B is a similarly derived "heat map" of a human HER2 polypeptide (SEQ ID NO:78) with a similar scale to graphically represent "hot spots" of epitopes displaying affinity for multiple MHC Class II molecules. FIG. 2C is a heat map of a 40 aa C-terminal neo-epitope of a human calreticulin (CALR) polypeptide (SEQ ID NO:79).

FIG. 3 is a graph plotting the average predicted affinities ($IC_{50}$) for cleavable 15-mer epitopes within SEA1, SEA2, VNTR1, and CMV pp65 polypeptides.

DETAILED DESCRIPTION

Figures 2C, 3:
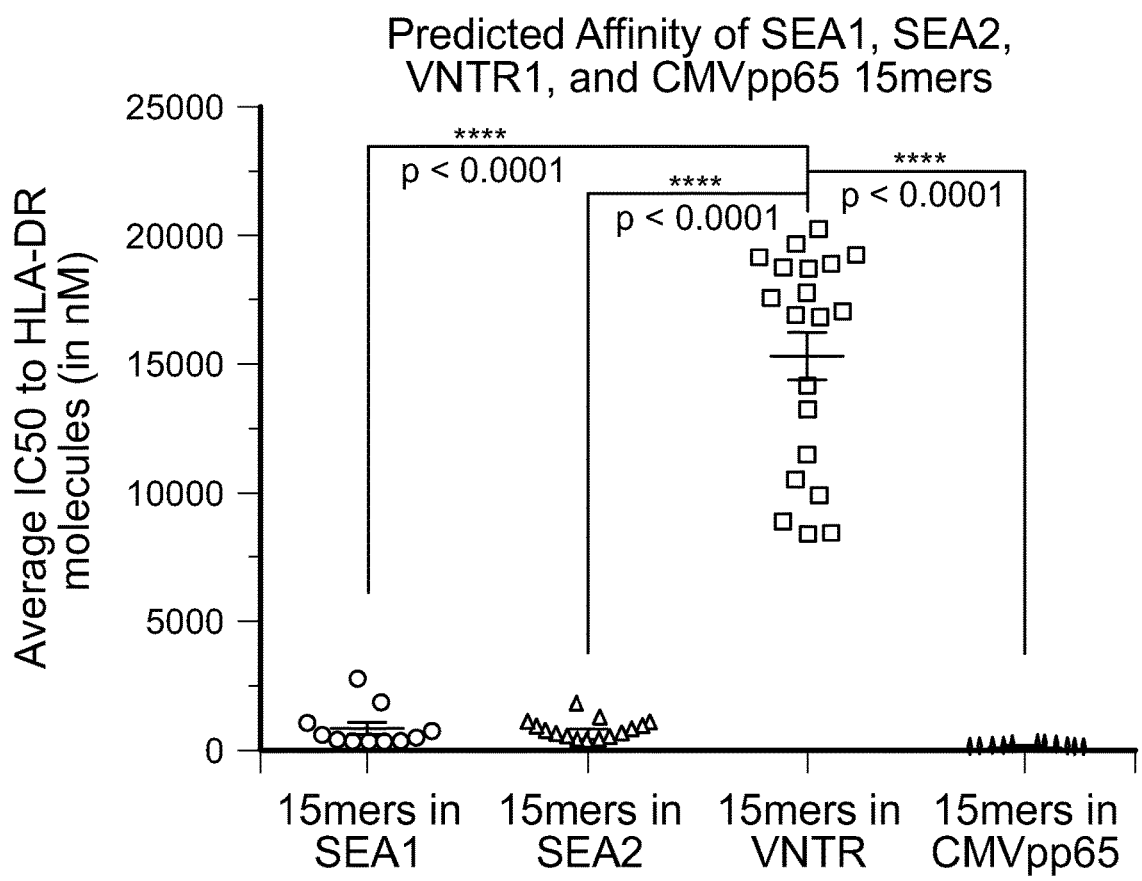

This document provides isolated polypeptides, polypeptide preparations, vaccine preparations (e.g., anti-cancer vaccine preparations), and methods for vaccinating mammals. For example, this document provides polypeptides that have the ability to be naturally processed and presented by different MHC molecules. In some cases, a polypeptide provided herein can have a sequence present in a cancer antigen polypeptide such as a MUC1, HER2, MESO, TRAG-3, or CALR polypeptide.

In general, a polypeptide provided herein is a fragment of a full-length polypeptide that is longer than 18 amino acid residues in length and shorter than the full length polypeptide. For example, a polypeptide provided herein can range from about 18 to about 55 (e.g., about 18 to about 50, about 20 to about 50, about 25 to about 50, about 30 to about 50, about 18 to about 45, about 18 to about 40, about 18 to about 35, about 20 to about 45, about 25 to about 40, or about 30 to about 35) amino acid residues in length. In some cases, a polypeptide provided herein can have the ability to induce immune responses in the context of multiple different MHC molecules. Examples of polypeptides provided herein include, without limitation, the polypeptides set forth in SEQ ID NOs:1-58 (Table 1).

TABLE 1

Examples of immunogenic polypeptides.

| SEQ ID NO: | Testing/ Details | Amino acid sequence (length) |
|---|---|---|
| 1 | */CMV pp65 | SQEPMSIYVYALPLKMLNIPSINVHHYP (28 aa) |
| 2 | MUC1 (N-terminus domain) | VPSSTEKNAVSMTSSVLSSHSPGSGSSTTQGQ (32 aa) |
| 3 | */MUC1 (degenerate repeat domain) | NRPALGSTAPPVHNVTSASGSASGSASTLV (30 aa) |
| 4 | MUC1 (degenerate repeat domain) | STAPPVHNVTSASGSASGSASTLVHNGTSARATTTPA (37 aa) |
| 5 | */MUC1 (SEA1 domain) | STSPQLSTGVSFFFLSFHISNLQFNSSLEDPSTD (34 aa) |
| 6 | */MUC1 (SEA2 domain) | STDYYQELQRDISEMFLQIYKQGGFLGLSNIKFRPGSVV (39 aa) |
| 7 | */MUC1 (SEA3 domain) | VHDVETQFNQYKTEAASRYNLTISDVSVSDVPFP (34 aa) |
| 8 | HER2 | MELAALCRWGLLLALLPPGAASTQVCT (27 aa) |

TABLE 1-continued

Examples of immunogenic polypeptides.

| SEQ ID NO: | Testing/ Details | Amino acid sequence (length) |
|---|---|---|
| 9 | HER2 | PASPETHLDMLRHLYQGCQVVQGNLELT (28 aa) |
| 10 | HER2 | VVQGNLELTYLPTNASLSFLQDIQEV (26 aa) |
| 11 | ¶/HER2 | LSFLQDIQEVQGYVLIAHNQVRQVPLQRL (29 aa) |
| 12 | ¶/HER2 | AHNQVRQVPLQRLRIVRGTQLFEDNYALA (29 aa) |
| 13 | ¶/HER2 | TEILKGGVLIQRNPQLCYQDTILWKDIFH (29 aa) |
| 14 | ¶/HER2 | YQDTILWKDIFHKNNQLALTLIDTNRSRACHPC (33 aa) |
| 15 | HER2 | LGMEHLREVRAVTSANIQEFAGC (23 aa) |
| 16 | ¶/HER2 | NIQEFAGCKKIFGSLAFLPESFDGDP (26 aa) |
| 17 | ¶/HER2 | VFETLEEITGYLYISAWPDSLPDLSV (26 aa) |
| 18 | ¶/HER2 | DLSVFQNLQVIRGRILHNGAYSLTLQGLG (29 aa) |
| 19 | HER2 | TLQGLGISWLGLRSLRELGSGLALIHHN (28 aa) |
| 20 | ¶/HER2 | ELGSGLALIHHNTHLCFVHTVPW (23 aa) |
| 21 | HER2 | HNTHLCFVHTVPWDQLFRNPH (21 aa) |
| 22 | HER2 | PSGVKPDLSYMPIWKFPDEEG (21 aa) |
| 23 | HER2 | EQRASPLTSIISAVVGILLVVV (22 aa) |
| 24 | ¶/HER2 | IKRRQQKIRKYTMRRLLQETELVEPLTPS (29 aa) |
| 25 | HER2 | QAQMRILKETELRKVKVLGSGAFGTVYK (28 aa) |
| 26 | ¶/HER2 | GVGSPYVSRLLGICLTSTVQLVTQLM (26 aa) |
| 27 | HER2 | DLLNWCMQIAKGMSYLEDVRL (21 aa) |
| 28 | HER2 | LEDVRLVHRDLAARNVLVKSP (21 aa) |
| 29 | ¶/HER2 | DLAARNVLVKSPNHVKITDFG (21 aa) |
| 30 | ¶/HER2 | DGGKVPIKWMALESILRRRFTHQS (24 aa) |
| 31 | HER2 | ESILRRRFTHQSDVWSYGV (19 aa) |
| 32 | HER2 | RLPQPPICTIDVYMIMVKCWMIDSECR (27 aa) |
| 33 | ¶/HER2 | SECRPRFRELVSEFSRMARDPQRFVVIQ (28 aa) |
| 34 | HER2 | ARDPQRFVVIQNEDLGPASP (20 aa) |
| 35 | MESO | ALGSLLFLLFSLGWVQPSRTLAGETGQ (27 aa) |
| 36 | MESO | GLSTERVRELAVALAQKNVKLSTEQLR (27 aa) |
| 37 | MESO | LDALPLDLLLFLNPDAFSGPQAC (23 aa) |
| 38 | MESO | FLNPDAFSGPQACTRFFSRITKANVDLLPRGAP (33 aa) |
| 39 | MESO | PSTWSVSTMDALRGLLPVLGQPIIRSIPQGIVAAWRQRSSRDPS (44 aa) |
| 40 | MESO | PSTWSVSTMDALRGLLPVLGQPIIRSIPQG (30 aa) |
| 41 | MESO | ALRGLLPVLGQPIIRSIPQGIVAAWRQRSSRDPS (34 aa) |
| 42 | MESO | PSTWSVSTMDALRGLLPVLGQPIIRSIPQGIVAAWRQRSSRDPS (44 aa) |

TABLE 1-continued

Examples of immunogenic polypeptides.

| SEQ ID NO: | Testing/ Details | Amino acid sequence (length) |
|---|---|---|
| 43 | MESO | QGYPESVIQHLGYLFLKMSPEDIRKWNVT (29 aa) |
| 44 | MESO | PEDIRKWNVTSLETLKALLEVNKGH (25 aa) |
| 45 | MESO | NMNGSEYFVKIQSFLGGAPTED (22 aa) |
| 46 | MESO | SQQNVSMDLATFMKLRTDAVLPLTVAEV (28 aa) |
| 47 | MESO | SQQNVSMDLATFMKLRTDAVLPLTVAE (27 aa) |
| 48 | MESO | DAVLPLTVAEVQKLLGPHVEGLKAE (25 aa) |
| 49 | MESO | GGIPNGYLVLDLSMQEALSGTPCLLGPGPV (30 aa) |
| 50 | TRAG-3 | MWMGLIQLVEGVKRKDQGFLE (21 aa) |
| 51 | TRAG-3 | GFLEKEFYHKTNIKMRCEFLACWPAFTVLGEA (32 aa) |
| 52 | TRAG-3 | DQVDWSRLLRDAGLVKMSRKPRASSPLSN (29 aa) |
| 53 | CALR neo-epitope | RRMMRTKMRMRRMRRTRRKMSPARPRTSCREACLQG WTEA (40 aa) |
| 54 | CALR neo-epitope | RRMMRTKMRMRRMRRTRRKMSPAR (24 aa) |
| 55 | CALR neo-epitope | RRMMRTKMRMRRMRRTRR (18 aa) |
| 56 | */MUC1 (SEA1 domain) | SPQLSTGVSFFFLSFHISNLQFNSSLEDPSTD (32 aa) |
| 57 | ¶/HER2 | GVGSPYVSRLLGICLTSTVQLV (22 aa) |
| 58 | MUC1-VNTR | AHGVTSAPDTRPAPGSTAPPAHGV (24 aa) |

* Represents polypeptides confirmed to be immunogenic in 4/4 healthy donors.
¶ Represents polypeptides confirmed to be immunogenic in one healthy donor.

The term "isolated" refers to material which is substantially or essentially free from components which normally accompany the material as it is found in its native state. Thus, isolated polypeptides as described in this document do not contain at least some of the materials normally associated with the polypeptides in their in situ environment. The term "polypeptide" refers to a chain of amino acids linked by polypeptide bonds.

Any appropriate method can be used to obtain a polypeptide provided herein. For example, polypeptides having the sequence set forth in any one of SEQ ID NOs:1-58 can be obtained using polypeptide synthesizing methods. In some cases, a polynucleotide sequence encoding a polypeptide provided herein can be inserted into a plasmid or other vector that can then be delivered to hosts that can be induced to transcribe and translate the polynucleotide into the polypeptide. In some cases, a polynucleotide sequence for a larger polypeptide can be inserted into host cells that can produce the larger polypeptide and then process that polypeptide into a smaller polypeptide or a functional variant of interest.

This document also provides compositions (e.g., anti-cancer vaccine compositions) containing one or more polypeptides provided herein. In some cases, a polypeptide provided herein can have the ability to be processed and presented by an MHC molecule. In some cases, the polypeptides set forth in SEQ ID NOs:1-58 can be used individually or as a mixture of two or more polypeptides to produce a composition (e.g., anti-cancer vaccine compositions). Any appropriate combination of the polypeptides listed in Table 1 can be used to produce a composition (e.g., anti-cancer vaccine compositions). For example, the combination can include at least 2, 3, 4, 5, 6, 7, 8, 9, 10, 11, 12, 13, 14, 15, 16, 17, 18, or more polypeptides selected from Table 1. For example, the polypeptides corresponding to SEQ ID NOs:2-7 can be used in any combination to produce an anti-cancer vaccine composition. In some cases, the polypeptides corresponding to SEQ ID NOs:2-7 and SEQ ID NOs:35-49 can be used in any combination to produce an anti-cancer vaccine composition. In some cases, a polypeptide having the amino acid sequence set forth in SEQ ID NO:2 and a polypeptide having the amino acid sequence set forth in SEQ ID NO:4 can be used together in any combination with one or more polypeptides of SEQ ID NOs:8-34 to produce an anti-cancer vaccine composition.

In some cases, a polypeptide provided herein (e.g., a polypeptide presented in Table 1) can include oxidized amino acid residues (e.g., oxidized forms of methionine) or can lack oxidized amino acid residues.

In some cases, a polypeptide provided herein (e.g., a polypeptide presented in Table 1) can include one or more modifications (e.g., post-translational modifications). Examples of post-translational modifications that can be present on a polypeptide provided herein include, without limitation, amidation (e.g., C-terminal amidation), acetylation (e.g., N-terminal acetylation), glycosylation, phosphorylation, and lipidation. For example, any one of SEQ ID NOs:1-58 can be amidated at the C-terminus and/or acetylated at the N-terminus. In cases where a mixture of two or more polypeptides provided herein are used, each polypeptide can be independently modified. For example, a combination of two or more of SEQ ID NOs:1-58 can include unmodified polypeptides, polypeptides amidated at the C-terminus, polypeptides acetylated at the N-terminus, and/or polypeptides amidated at the C-terminus and acetylated at the N-terminus.

A composition provided herein containing one or more polypeptides set forth in SEQ ID NOs:1-58 or any appropriate combination of polypeptides as described herein can be formulated to provide a polypeptide-based, anti-cancer vaccine. Any appropriate method can be used to formulate a polypeptide-based vaccine including, for example, those methods used to formulate polypeptide-based vaccines directed against other targets. Examples of polypeptide-based vaccines directed to other targets are described elsewhere (see, e.g., Belyakov et al., *Proc. Natl. Acad. Sci. U.S.A.*, 95(4):1709-1714 (1998) and Jackson et al., *Proc. Natl. Acad. Sci. U.S.A.*, 101(43):15440-15445 (2004)).

In some cases, a composition provided herein can be designed to treat cancer or a precancerous condition. For example, a composition (e.g., a vaccine composition) provided herein can have the ability to induce a therapeutic immune response against cancer cells within a mammal (e.g., a human). For example, a composition provided herein can have the ability to activate and, optionally, expand T-cells obtained from a mammal (e.g., a human) in culture.

A polypeptide provided herein (e.g., a polypeptide set forth in Table 1) can be formulated into a vaccine composition using any appropriate method. In some cases, a polypeptide provided herein can be combined with a pharmaceutically acceptable carrier or pharmaceutical excipient. The term "pharmaceutically acceptable" refers to a generally non-toxic, inert, and/or physiologically compatible composition. A term "pharmaceutical excipient" includes materials such as adjuvants, carriers, pH-adjusting and buffering agents, tonicity adjusting agents, wetting agents, preservatives, and the like. Examples of adjuvants include, without limitation, CpG, aluminum sulfate, aluminumphosphylate, MF59, Pam3CSK4, LPS, polyIC, imiquimod, and R848. In some cases, vaccines or components of a vaccine can be conjugated to, for example, a polysaccharide or other molecule, to improve stability or immunogenicity of one or more vaccine components. In some cases, a polypeptide provided herein (e.g., a polypeptide set forth in Table 1) can be formulated into a vaccine composition containing cells. For example, one or more polypeptides provided herein can be included within a cellular vaccine. Any appropriate method can be used to prepare a cellular vaccine or the components of a cellular vaccine.

This document also provides methods and materials (e.g., vaccines) for treating cancer or a precancerous condition. For example, the vaccines provided herein can include one or more of the cancer antigen polypeptides provided herein and can have the ability to induce a therapeutic immune response against cancer cells within a mammal (e.g., a human). For example, the compositions provided herein can include one or more of the cancer antigen polypeptides provided herein and can have the ability to activate and, optionally, expand T-cells obtained from a mammal (e.g., a human) in culture. Activated T-cells can be used in an immunotherapy (e.g., adoptive T-cell therapy), and can be administered to a mammal (e.g., a human) to induce a therapeutic immune response against cancer cells within the mammal. Any appropriate type of cancer can be treated using the methods and materials provided herein. For example, breast cancer, pancreatic cancer, ovarian cancer, stomach cancer, lung cancer, colon cancer, multiple myeloma, leukemia, brain cancer, and melanoma cancer can be treated using the methods and materials provided herein. Any appropriate type of precancerous condition can be treated using the methods and materials provided herein. For example, myelofibrosis (e.g., primary myelofibrosis), essential thrombocythemia, and polycythemia vera can be treated using the methods and materials provided herein.

In some cases, a composition provided herein (e.g., an anti-cancer vaccine composition) can be administered to a mammal having cancer or a precancerous condition under conditions effective to reduce the severity of one or more symptoms of the cancer or precancerous condition and/or to reduce the number of cancer cells or precancerous cells present within the mammal. Treatment of individuals having cancer or a precancerous condition can include the administration of a therapeutically effective amount of one or more polypeptides provided herein (e.g., one or more of SEQ ID NOs:1-58). In some cases, treatment can include the use of one or more polypeptides set forth in SEQ ID NOs:1-58 individually or as a mixture. The polypeptides can be used or administered as a mixture, for example, in equal amounts, or individually, provided in sequence, or administered all at once. The term "therapeutically effective amount" as used with treating cancer or a precancerous condition refers to that amount of the agent sufficient to reduce one or more symptoms of the cancer of precancerous condition and/or to reduce the number of cancer cells or precancerous cells within a mammal. In providing a subject with a polypeptide provided herein (e.g., an anti-cancer vaccine composition) capable of inducing a therapeutic effect, the amount of administered agent will vary depending upon such factors as the subject's age, weight, height, sex, general medical condition, previous medical history, etc. The subject can be, for example, a mammal. The mammal can be any type of mammal including, without limitation, a mouse, rat, dog, cat, horse, sheep, goat, cow, pig, monkey, or human.

The invention will be further described in the following examples, which do not limit the scope of the invention described in the claims.

EXAMPLES

Example 1—Identification of Long Polypeptides Having Promiscuous MHC Binding Capabilities There are two classes of MHC molecules: MHC Class I and Class II that are involved in presentation of epitopes to T-cells. $CD8^+$ T-cells recognize epitopes that are typically 8-12 amino acids long, on MHC Class I. $CD4^+$ T-cells recognize epitopes that are typically 15-20 amino acids long, on MHC Class II. In order for T-cells to recognize these epitopes, the epitopes have to remain bound to MHC molecules, meaning that the affinity of epitopes for MHC molecules limits which epitopes are part of an immune response.

Within MHC Class I, there are three gene loci, HLA-A, -B, and -C that determine the protein sequence for these MHC Class I molecules, and thus the epitopes that are part of an immune response. While there is genetic diversity in these loci, within the HLA-A locus specifically, nearly 50% of the population has the same gene, HLA-A2. One can identify epitopes that bind to HLA-A2 and use these peptides to therapeutically treat HLA-A2 positive cancer patients, either as part of a vaccine or in another modality.

The MHC Class II gene loci, HLA-DP, -DQ, and -DR are much more genetically diverse. Of these loci, HLA-DR is the most studied, and its role in the presentation of epitopes to $CD4^+$ T-cells is best understood. HLA-DP and -DQ may have more specific roles that are not well suited for all situations where epitopes are presented to $CD4^+$ T-cells. Within the DR locus, the significant genetic diversity is attributable to diversity of HLA-DRB1 genes. Furthermore, specific HLA-DRB1 genes are associated with additional HLA-DRB genes (HLA-DRB3,4,5), which further diversify the repertoire of MHC Class II molecules in the population.

The strategy employed by HLA-A2 epitope identification may not work for HLA-DR; epitopes should bind to multiple HLA-DR types in order to be used rationally to treat cancer patients.

Initial investigations utilized a binding prediction algorithm SYFPEITHI, which scans only six HLA-DR types (HLA-DRB*0101, *0301, *0401, *0701, *1101 & *1501) and assigns arbitrary scores to epitopes based upon amino acids that are known to assist in the binding to MHC molecules. As an example, shown in FIG. 1, the entire sequence of the tumor associate antigen MUC1 was analyzed. Sequences underlined and labeled with ("#") were predicted to be binders to the HLA-DR types analyzed by SYFPEITHI. Scores shown are averages across the HLA-DR types+/− standard deviation. A few critical limitations of this method were identified:

1. The method predicted a large number of epitopes, which would limit throughput and the ability to rationally test all epitopes.

2. The method did not adequately delineate between epitopes in order to determine which should be stronger binders amongst the identified epitopes.
3. Most importantly, it did not encompass a wide enough cross section of HLA types to rationally treat enough patients.

Due to the large number HLA-DR types, it would be onerous to examine all of them to assess, which epitopes bind to the most HLA-DR types. The following was performed to rationally limit the investigation to HLA-DRB1, due to the fact that it is the most well studied HLA-DR molecule, epitope binding prediction algorithms were largely trained on HLA-DRB1 molecules, and the fact that HLA-DRB3, 4, and 5 only occur in conjunction with specific HLA-DRB1 genes.

Utilizing previously published data, the HLA-DRB1 diversity across multiple global ethnic groups resident within the United States was systematically examined. The goal was to ensure that nearly 9 in 10 patients across the seven main ethnic/racial groups would have HLA-DRB1 coverage. The following steps recapitulate the methodology:

1. HLA-DRB1 alleles with greater than 6% frequency in 1 or more population groups were chosen.
2. HLA-DRB1 alleles with greater than 3% frequency in 2 or more population groups were chosen.
3. HLA-DRB1 alleles with greater than 1.5% frequency in 3 or more population groups were chosen.
4. For population groups with less than 89.0% coverage, add next highest allele frequencies for that group, until 89% coverage.

As indicated in Table 2, 29 different HLA-DRB1 types were chosen that covered nearly 90% of each population, thus ensuring that nearly 9/10 people in the United States could respond. This level of population coverage was unattainable using other technologies.

TABLE 2

Identification of HLA-DR Alleles Across Races and Ethnicities

| DRB1 Alleles | African American Frequency | Caucasian Frequency | Chinese Frequency | Hispanic Frequency | Indian Frequency | Japanese Frequency | Korean Frequency |
|---|---|---|---|---|---|---|---|
| 0101 | 2.65% | 8.60% | 0.93% | 4.33% | 3.21% | 5.84% | 5.78% |
| 0102 | 3.92% | 1.38% | 0.07% | 3.32% | 0.13% | 0.06% | 0.02% |
| 0301 | 6.99% | 12.16% | 6.81% | 6.95% | 7.46% | 0.66% | 2.20% |
| 0302 | 6.31% | 0.03% | 0.00% | 0.50% | 0.01% | 0.01% | 0.00% |
| 0401 | 2.02% | 5.78% | 0.51% | 1.61% | 0.90% | 1.15% | 0.78% |
| 0403 | 0.17% | 0.79% | 2.31% | 1.84% | 5.27% | 2.43% | 2.57% |
| 0404 | 0.82% | 3.88% | 0.88% | 5.76% | 2.01% | 0.32% | 1.39% |
| 0405 | 1.53% | 0.67% | 6.12% | 2.22% | 0.75% | 14.72% | 6.94% |
| 0407 | 0.39% | 1.12% | 0.08% | 7.47% | 0.13% | 0.64% | 0.44% |
| 0701 | 10.11% | 13.42% | 5.31% | 9.61% | 16.95% | 0.94% | 7.15% |
| 0802 | 0.09% | 0.08% | 0.55% | 9.84% | 0.51% | 4.34% | 2.50% |
| 0803 | 0.04% | 0.24% | 6.80% | 0.27% | 0.71% | 7.44% | 7.62% |
| 0804 | 5.42% | 0.20% | 0.01% | 0.68% | 0.08% | 0.02% | 0.00% |
| 0901 | 2.97% | 1.03% | 15.54% | 0.82% | 0.94% | 13.87% | 9.67% |
| 1001 | 1.92% | 0.85% | 1.34% | 1.30% | 6.28% | 0.40% | 1.70% |
| 1101 | 8.54% | 5.56% | 6.26% | 3.55% | 5.96% | 2.58% | 4.73% |
| 1104 | 0.58% | 2.95% | 0.25% | 3.25% | 1.97% | 0.12% | 0.07% |
| 1201 | 3.82% | 1.64% | 3.42% | 0.91% | 0.80% | 3.75% | 4.83% |
| 1202 | 0.29% | 0.02% | 11.50% | 0.15% | 2.99% | 1.71% | 3.45% |
| 1301 | 5.42% | 5.63% | 0.78% | 3.72% | 6.73% | 0.76% | 1.73% |
| 1302 | 7.30% | 4.88% | 2.42% | 3.50% | 3.37% | 5.75% | 8.62% |
| 1303 | 3.26% | 1.09% | 0.02% | 1.06% | 0.13% | 0.04% | 0.01% |
| 1401 | 1.85% | 2.61% | 3.33% | 1.84% | 1.13% | 3.01% | 2.68% |
| 1404 | 0.05% | 0.07% | 0.51% | 0.03% | 7.13% | 0.02% | 0.06% |
| 1408 | 0.01% | 0.02% | 0.02% | 4.27% | 0.05% | 1.42% | 0.68% |
| 1501 | 2.82% | 13.46% | 10.12% | 6.43% | 9.02% | 8.67% | 7.94% |
| 1502 | 0.23% | 0.72% | 2.66% | 1.17% | 10.73% | 9.67% | 3.18% |
| 1503 | 11.66% | 0.05% | 0.00% | 0.58% | 0.02% | 0.01% | 0.00% |
| 1602 | 1.38% | 0.15% | 4.35% | 2.47% | 0.67% | 0.67% | 0.99% |
| Total Coverage | 92.6% | 92.1% | 92.9% | 89.4% | 95.8% | 91.0% | 89.7% |

In order to examine this number of HLA-DRB1 molecules, different binding algorithm predictors were used. The netMHCII-pan-2.1 and -3.0 algorithms, which can make binding affinity predictions for the 29 HLA-DRB1 molecules under study (Nielsen et al., *Immunome Res.*, 6:9 (2010), and Karosiene et al., *Immunogenetics*, 65(10):711-724 (2013)) were chosen. Unlike SYFPEITHI, these predictors provided $IC_{50}$ binding affinities, allowing for a quantitative assessment of whether or not the 15-mers are likely to be bound to HLA-DRB1 molecules. Utilizing 500 nM or 750 nM as $IC_{50}$ binding cut offs, each full length cancer-associated polypeptide (MUC1, HER2, MESO, TRAG-3, and CALR) was scanned for binding to the 29 different HLA-DRB1 molecules.

This method allowed one to solve the first two problems by reducing the number of epitopes needed for study and allowing one to better rank and rationally evaluate the different epitopes. For example, compared to the SYFPEITHI analysis, no HLA-DRB1 binding epitopes were identified within the variable number of tandem repeats (VNTR) domain of MUC1, a region that has been extensively studied. This increases throughput, reduces cost, and allows for more rational experimental designs.

Furthermore, the method provided additional granularity for determining epitopes that are more promiscuous or better binders than others. While almost all the epitopes were comparable to one another in the SYFPEITHI analysis, this new methodology clearly demonstrated that there are high value and low value epitopes within MUC1. An example of this is the SEA2 polypeptide, which contains the greatest density of extremely promiscuous epitopes, such that in the entire polypeptide there is at least one epitope that binds to all 29 HLA-DR molecules studied (Table 3). This level of prioritizing and being able to rationally rank targets is substantial compared to other methods.

In addition, the challenge of HLA-DR diversity in preventing the rational treatment of cancer patients was overcome. This is largely due to focusing on a greater number of HLA-DR molecules, but it was also due to the unexpected clustering of these promiscuous epitopes around one another within the polypeptide sequence. Many of these promiscuously binding epitopes within a polypeptide region were found to bind to a different set of HLA-DRB1 genes than the other epitopes within that region. This represents a lead break through, allowing for regions of polypeptides that are binders for 90% of the population, even if each epitope within that region does not have the same degree of promiscuity.

Additionally, many of the polypeptides described herein, with 90% population coverage for MHC Class II, contained predicted HLA-A2 epitopes. This discovery allows for the rational targeting of both MHC Class I and Class II, with the potential to synthesize one or more long polypeptides (e.g., from 20 to 50 amino acid polypeptides) that encompass these epitopes and rationally treat cancer patients.

TABLE 3

SEA2

| SEQ ID NO | Embedded 15 mers | Predicted Binding HLA-DRB1 Molecules | #Binders/Total |
|---|---|---|---|
| 59 | DYYQELQRDISEMFL | 01.01, 01.02, 03.01, 03.02, 04.01, 04.05, 07.01, 08.03, 09.01, 10.01, 11.01, 11.04, 12.01, 12.02, 13.01, 13.02, 13.03, 14.06 | 18/29 |
| 60 | YYQELQRDISEMFLQ | 01.01, 01.02, 03.01, 03.02, 04.01, 04.05, 07.01, 08.03, 09.01, 10.01, 11.01, 11.04, 12.01, 12.02, 13.01, 13.02, 13.03, 14.06 | 18/29 |
| 61 | YQELQRDISEMFLQI | 01.01, 01.02, 03.01, 03.02, 04.01, 04.05, 07.01, 08.03, 09.01, 11.04, 12.01, 12.02, 13.01, 13.02, 13.03, 14.06 | 16/29 |
| 62 | DISEMFLQIYKQGGF | 01.01, 01.02, 04.04, 04.05, 07.01, 08.03, 08.04, 10.01, 11.01, 11.04, 12.01, 12.02, 13.03, 14.04, 14.05, 15.01, 15.03, 16.02 | 18/29 |
| 63 | ISEMFLQIYKQGGFL | 01.01, 01.02, 04.01, 04.04, 04.05, 07.01, 08.03, 08.04, 09.01, 10.01, 11.01, 11.04, 12.01, 12.02, 13.02, 13.03, 14.04, 14.08, 15.01, 15.02, 15.03, 16.02 | 22/29 |
| 64 | SEMFLQIYKQGGFLG | 01.01, 01.02, 04.01, 04.04, 04.05, 07.01, 08.03, 08.04, 09.01, 10.01, 11.01, 11.04, 12.01, 12.02, 13.01, 13.03, 14.01, 14.04, 14.06, 15.01, 15.02, 15.03, 16.02 | 23/29 |
| 65 | EMFLQIYKQGGFLGL | 01.01, 01.02, 04.01, 04.04, 04.05, 07.01, 08.03, 08.04, 09.01, 10.01, 11.01, 11.04, 12.01, 12.02, 13.01, 13.03, 14.01, 14.04, 14.06, 15.01, 15.02, 15.03, 16.02 | 23/29 |
| 66 | MFLQIYKQGGFLGLS | 01.01, 01.02, 04.01, 04.04, 04.05, 07.01, 08.03, 08.04, 09.01, 10.01, 11.01, 11.04, 12.01, 12.02, 13.01, 13.03, 14.01, 14.04, 14.06, 15.01, 15.02, 15.03, 16.02 | 23/29 |
| 67 | FLQIYKQGGFLGLSN | 01.01, 01.02, 07.01, 08.03, 08.04, 09.01, 10.01, 11.01, 11.04, 12.01, 12.02, 13.01, 13.03, 14.04, 14.06, 15.01, 15.02, 15.03, 16.02 | 19/29 |
| 68 | LQIYKQGGFLGLSNI | 01.01, 01.02, 04.01, 04.05, 07.01, 08.03, 08.04, 09.01, 10.01, 11.01, 11.04, 12.01, 12.02, 13.01, 13.03, 14.06, 15.01, 15.03, 16.02 | 19/29 |
| 69 | QIYKQGGFLGLSNIK | 01.01, 01.02, 04.01, 04.05, 08.03, 09.01, 10.01, 11.01, 11.04, 12.01, 12.02, 13.01, 13.03, 14.06, 15.01, 15.02, 15.03, 16.02 | 18/29 |
| 70 | IYKQGGFLGLSNIKF | 01.01, 01.02, 04.01, 04.04, 04.05, 07.01, 08.03, 09.01, 10.01, 11.01, 11.04, 12.01, 12.02, 13.03, 14.04, 14.06, 15.01, 15.02, 15.03, 16.02 | 20/29 |
| 71 | YKQGGFLGLSNIKFR | 01.01, 01.02, 04.01, 04.04, 04.05, 04.07, 07.01, 08.03, 08.04, 09.01, 10.01, 11.01, 11.04, 12.01, 12.02, 13.01, 13.02, 13.03, 14.04, 14.06, 15.01, 15.02, 15.03, 16.02 | 24/29 |
| 72 | KQGGFLGLSNIKFRP | 01.01, 01.02, 03.01, 04.01, 04.03, 04.04, 04.05, 04.07, 07.01, 08.03, 08.04, 09.01, 10.01, 11.01, 11.04, 12.01, 12.02, 13.03, 14.04, 14.06, 15.01, 15.02, 15.03, 16.02 | 24/29 |
| 73 | QGGFLGLSNIKFRPG | 01.01, 01.02, 04.01, 04.04, 04.05, 04.07, 07.01, 08.03, 08.04, 09.01, 10.01, 11.01, 11.04, 12.01, 12.02, 13.03, 14.04, 14.06, 15.01, 15.02, 15.03, 16.02 | 21/29 |
| 74 | GFLGLSNIKFRPGSV | 01.01, 01.02, 04.01, 04.04, 04.05, 07.01, 08.02, 08.03, 08.04, 09.01, 10.01, 11.01, 11.04, 12.01, 12.02, 13.01, 13.02, 13.03, 14.04, 14.06, 15.01, 15.02, 15.03, 16.02 | 24/29 |
| 75 | FLGLSNIKFRPGSVV | 01.01, 01.02, 04.01, 04.04, 07.01, 08.02, 08.03, 08.04, 09.01, 11.01, 11.04, 12.01, 12.02, 13.01, 13.02, 13.03, 14.04, 14.06, 15.01, 15.03, 16.02 | 21/29 |

The nature distribution of these clusters allowed for a graphical representation of the discovery, utilizing an intelligent "heat map" of activity. For each MHC Class II epitope (generally considered to be 15 amino acids long) within the entire polypeptide, a shading was assigned on a 29 shading gradient scale between light to dark depending on the number of HLA-DRB1 molecules that the epitope was predicted to bind to out of the 29 tested (using the predicted nM affinities). Epitopes with no predicted binding to any HLA-DRB1 molecules remained light, while a 29/29 was dark (e.g., "hot"). The amino acid at the N-terminus of the epitope bears the shade assigned for that epitope. This analysis allowed for a graphical representation of a polypeptide's immunologic "hot spots." The immunological hot spots for MUC1, HER2/neu, and a myelofibrosis-associated CALR C-terminal epitope are shown in FIGS. 2A, 2B, and 2C. The 40 aa C-terminus of CALR is a neo-epitope that is not present on CALR of healthy individuals, but is present on CALR in 80% of pre-leukemic patients.

For MUC1, the VNTR polypeptide (FIG. 2A, uppermost box) lacked hot spots in contrast to two hot polypeptides (next two boxes) designated as the SEA1 and SEA2 regions. For both MUC1 and HER2, the final 14 amino acids lacked hot spots because the sequences were too short to have a 15-mer epitope that begins with them. With this methodology, long polypeptides (e.g., longer than 20 amino acid residues) were successfully identified for several cancer-associated antigens (e.g., MUC1, HER2/neu, MESO, TRAG-3, and CALR) as containing a high density of promiscuous HLA-DR 15-mer epitopes.

To test the reliability of these results, the immune responses for MUC1 long polypeptides (SEA1 and SEA2) were compared to that generated using a pathogen polypeptide. To do this, the same identification methodology used for the tumor antigen polypeptides was used to identify hot spots in the cytomegalovirus (CMV) pp65 polypeptide. The hot spot sequence that was identified was used as a control as was the previously identified VNTR polypeptide. As shown in FIG. 3, the predicted average binding affinity across the 29 HLA-DRB1 genes for the 15-mer epitopes within the VNTR polypeptide was extremely high (in this case lower represents a lower amount of polypeptide needed to bind, and thus better), whereas the 15-mers embedded in the CMV long polypeptide, SEA1, and SEA2 were extremely low, thus meaning that the epitopes within CMV pp65, SEA1, and SEA2 are much tighter binders.

Figure 4A:
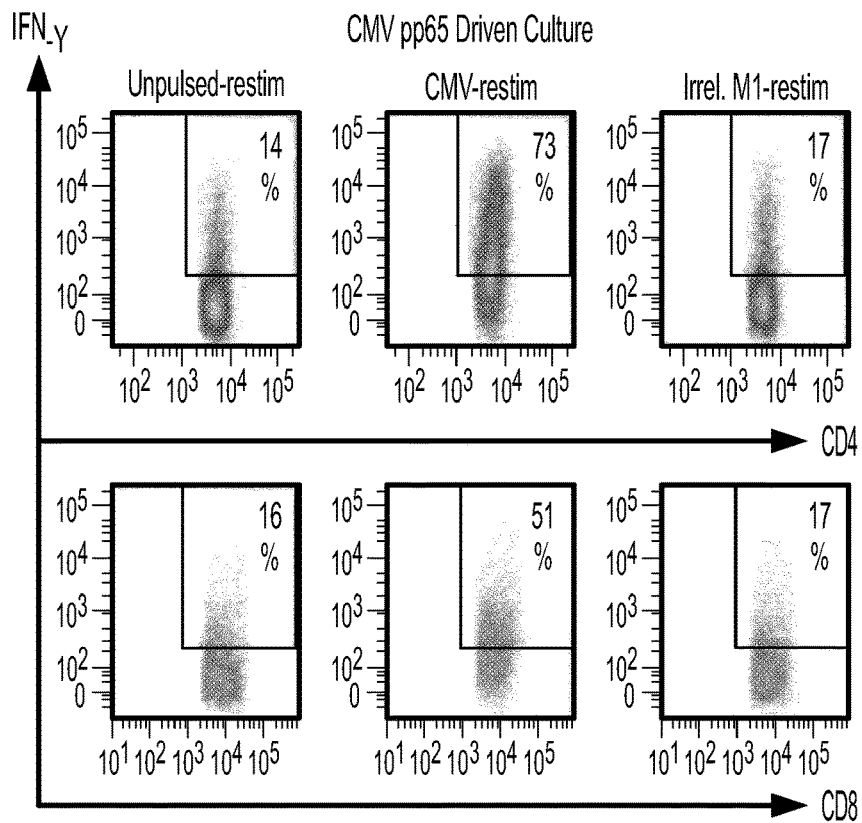
FIG. 4A is a dot plot from an intracellular cytokine assay, plotting interferon gamma (IFNγ) levels of T-cells in response to different restimulatory conditions after T-cell cultures were initially stimulated with the CMV pp65 polypeptide. To control for background levels of IFNγ, T-cells were tested against a lack of polypeptide or an irrelevant MUC1 polypeptide.
Figure 4B:
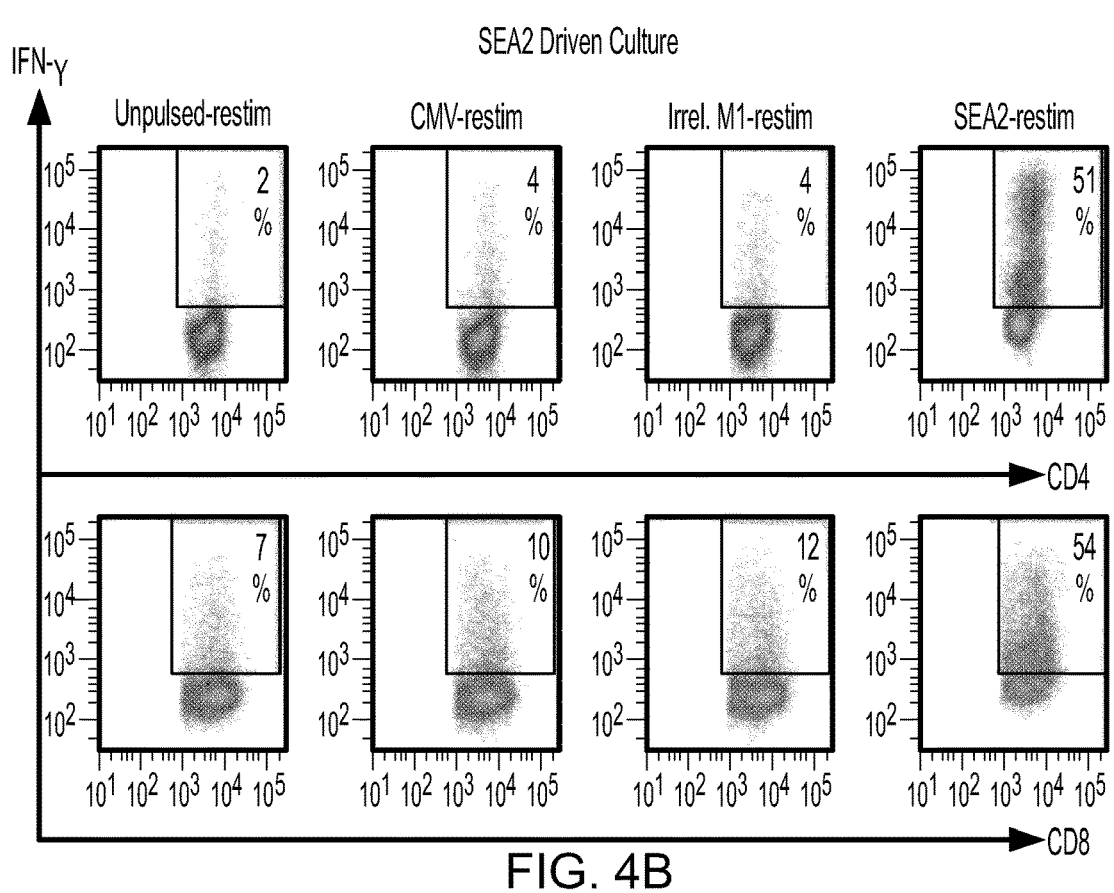
FIG. 4B is a dot plot from an intracellular cytokine assay plotting IFNγ levels of T-cells in response to different restimulatory conditions after T-cell cultures were initially stimulated with the SEA2 polypeptide. To control for background levels of IFNγ, T-cells were tested against a lack of polypeptide or an irrelevant CMV and irrelevant MUC1 polypeptide.
Figure 4C:
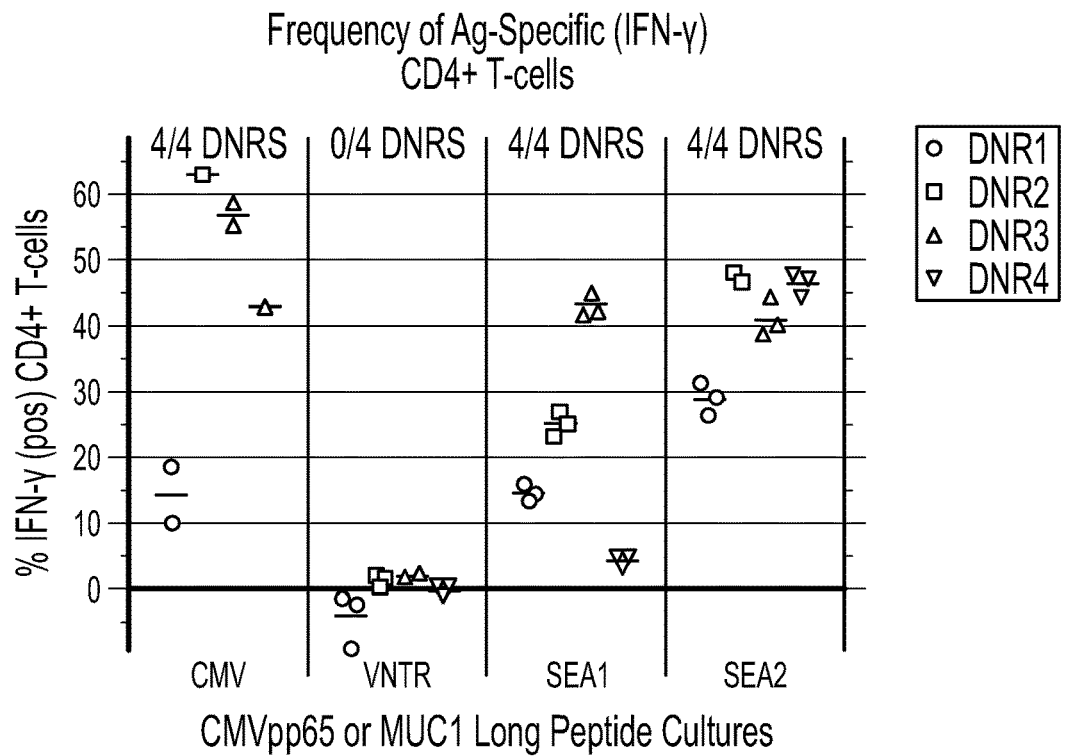
FIGS. 4C and 4D are graphs plotting the frequency of antigen-specific $CD4^+$ T cells and $CD8^+$ T cells, respectively, as measured by the percentage of T-cells, which secrete antigen-specific IFNγ. Briefly, T-cell cultures from four different healthy donors were initially stimulated with one of four polypeptides, CMV pp65, VNTR1, SEA1, or SEA2. At the end of culture, T-cells were restimulated with the original polypeptide and other irrelevant polypeptides or no polypeptide. Each data point represents the level of IFNγ after subtracting the levels of IFNγ from restimulation with irrelevant polypeptides or no polypeptide from levels when T-cells were restimulated with the original polypeptide.

The SEA polypeptides, CMV long polypeptide, and VNTR polypeptide were tested in a culture system. Briefly, bulk peripheral blood mononuclear cells (PBMC) were thawed and exposed to GM-CSF on day 0 in culture. On day 1, cultures were exposed to the polypeptides (SEA1, SEA2, CMV pp65, or VNTR) and monocyte maturating agents (LPS and R848). On day 2, media was washed out, and the cells were split 1:6 in fresh media containing IL-7 for T-cell expansion. Further splits occurred with simple addition of more media containing IL-7 depending upon acidity of the media between days 7-15. On day 16, an antigen specific restimulation of T-cell cultures was performed utilizing fresh PBMC as the antigen presenting cells. These fresh PBMC were thawed on day 14 and treated the same way as the initial culture on days 0-1, before being used on day 16. At the time of restimulation, an intracellular cytokine assay was performed. The T-cell cultures also were allowed to proliferate for an additional 14 days in media containing IL-7. At the end of culture, day 28, T-cells were further tested with a new intracellular cytokine assay utilizing fresh PBMC, prepared the same way as the PBMC used on day 16 for the first intracellular cytokine assay. Representative dot-plots for IFNγ levels are shown for the CMV pp65 polypeptide and the SEA2 polypeptide, with levels being much lower when T-cells were not restimulated with the same polypeptide they saw at the initiation of culture. As shown in FIGS. 4C and D, in contrast to the VNTR polypeptide, the CMV long polypeptide, SEA1 long polypeptide, and SEA2 long polypeptide consistently exhibited an immune response by antigen specific IFNγ production. Each data point represents the level of IFNγ after subtracting the levels of IFNγ from restimulation with irrelevant polypeptides or no polypeptide from levels when T-cells were restimulated with the original polypeptide.

Other polypeptides as indicated in Table 1 were tested and confirmed to produce detectable immune responses.

Example 2—Expansion of CD4$^+$ and CD8$^+$ T-Cells with Enriched Specificity for Tumor-Associated Long Synthetic Polypeptides Whether GM+R848+LPS conditioned PBMC could process exogenous synthetic peptides as effectively as *Candida albicans* extract (CAN) or recombinantly produced HER2-ICD was examined.

The following long peptides were synthesized for immunotargeting:
 CMVpp65-derived 28mer (SQEPMSIYVY-ALPLKMLNIPSINVHHYP; SEQ ID NO:1)
 MUC1-SEA domain-derived 32mer (SEA1; SPQLSTGVSFFFLSFHISNLQFNSSLEDPSTD-amide; the amino acid sequence of which is set forth in SEQ ID NO:56, with a C-terminal amidation) MUC1-SEA domain-derived 39mer (SEA2; STDYYQELQRDISEMFLQIYKQGGFLGL-SNIKFRPGSVV-amide; SEQ ID NO:6 with a C-terminal amidation)
 HER2 p146-174 29mer (TEILKGGVLIQRNPQL-CYQDTILWKDIFH; SEQ ID NO:13)
 HER2 p848-865 21mer (DLAARNVLVK-SPNHVKITDFG; SEQ ID NO:29)
 HER2 p675-703 29mer (IKRRQQKIRKYTMRRLLQETELVEPLTPS; SEQ ID NO:24)
 HER2 p776-797 22mer (GVGSPYVSRLLGICLT-STVQLV; SEQ ID NO:57)
 MUC1-VNTR 24mer (AHGVTSAPDTRPAPGSTAP-PAHGV-amide; the amino acid sequence of which is set forth in SEQ ID NO:58, with a C-terminal amidation) also was synthesized as a control for its contrastingly low predicted affinities for HLA-DR and A2.1 (FIG. 3). All peptides were produced to >98% homogeneity as confirmed by mass spectroscopy.

Figure 4D:
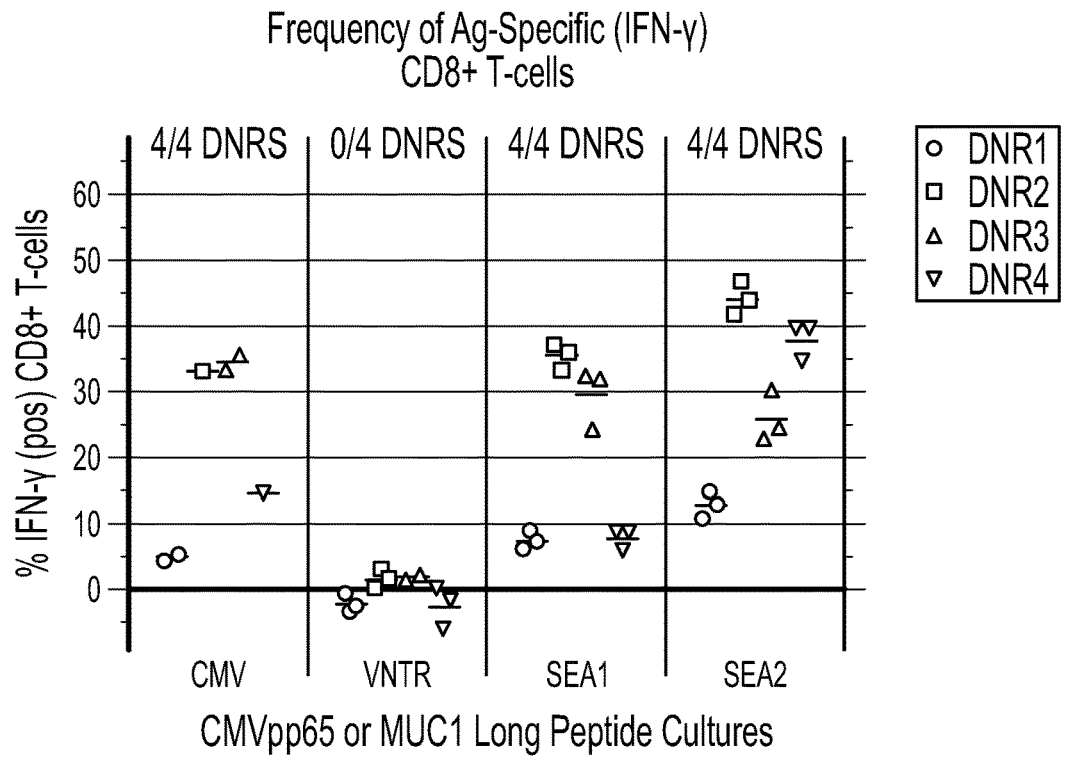
Figure 5A:
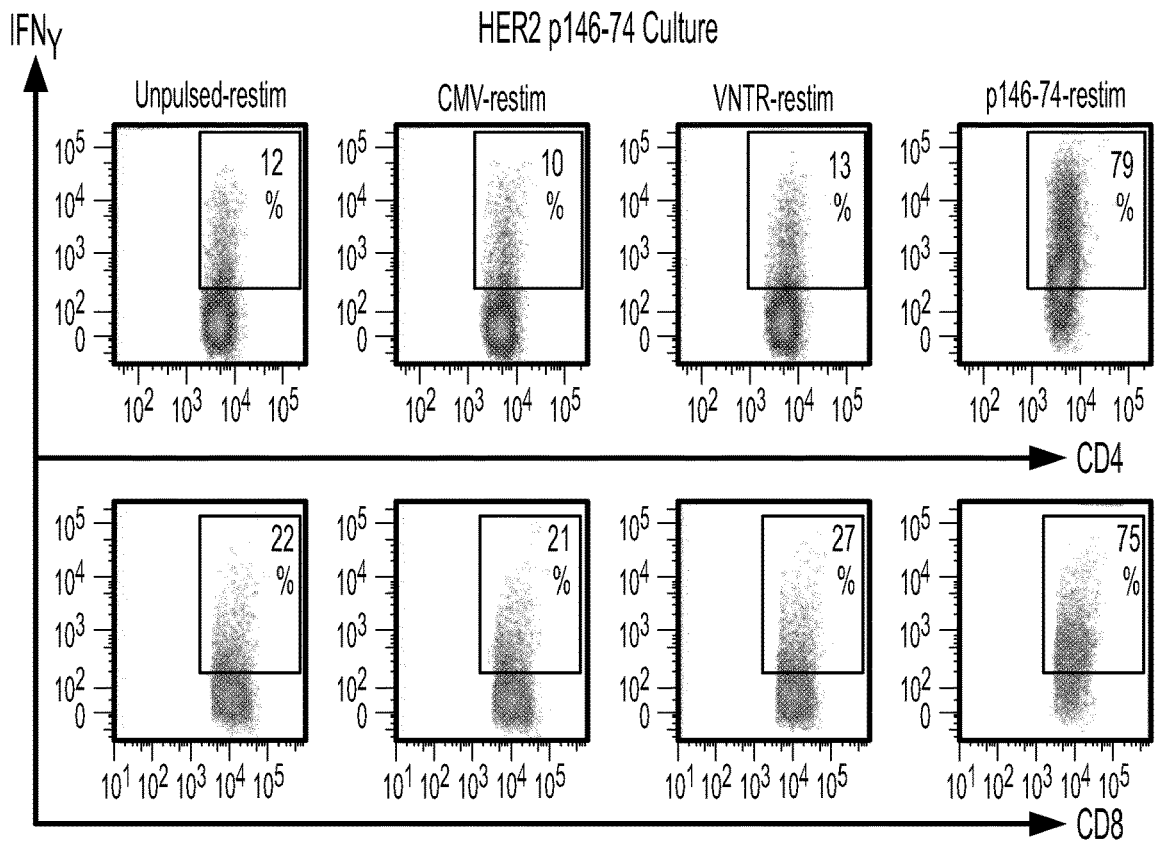
FIG. 5A is a dot plot from an intracellular cytokine assay, plotting IFNγ levels of T-cells in response to different restimulatory conditions after T-cell cultures were initially stimulated with the HER2/neu-derived p146-74 peptide sequences.
Figure 5B:
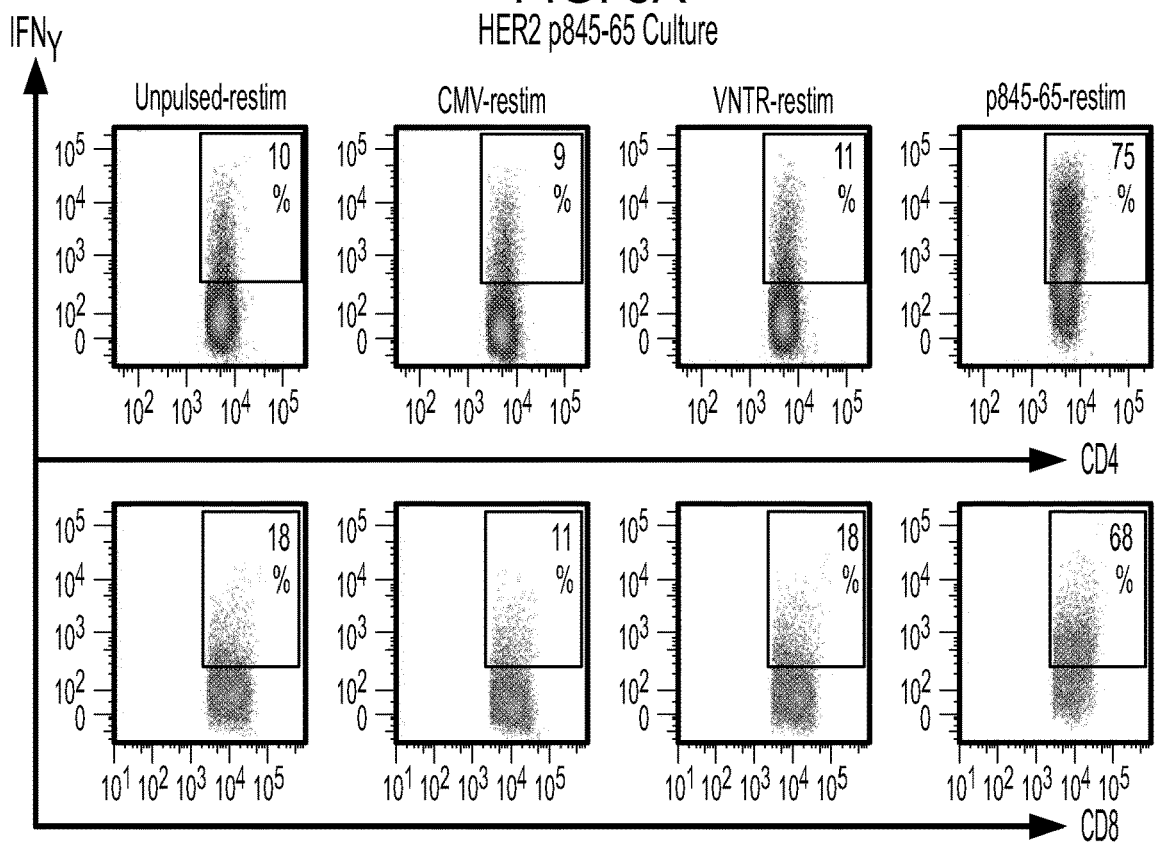
FIG. 5B is a dot plot from an intracellular cytokine assay, plotting IFNγ levels of T-cells in response to different restimulatory conditions after T-cell cultures were initially stimulated with the HER2/neu-derived p845-65 peptide sequences.
Figure 5C:
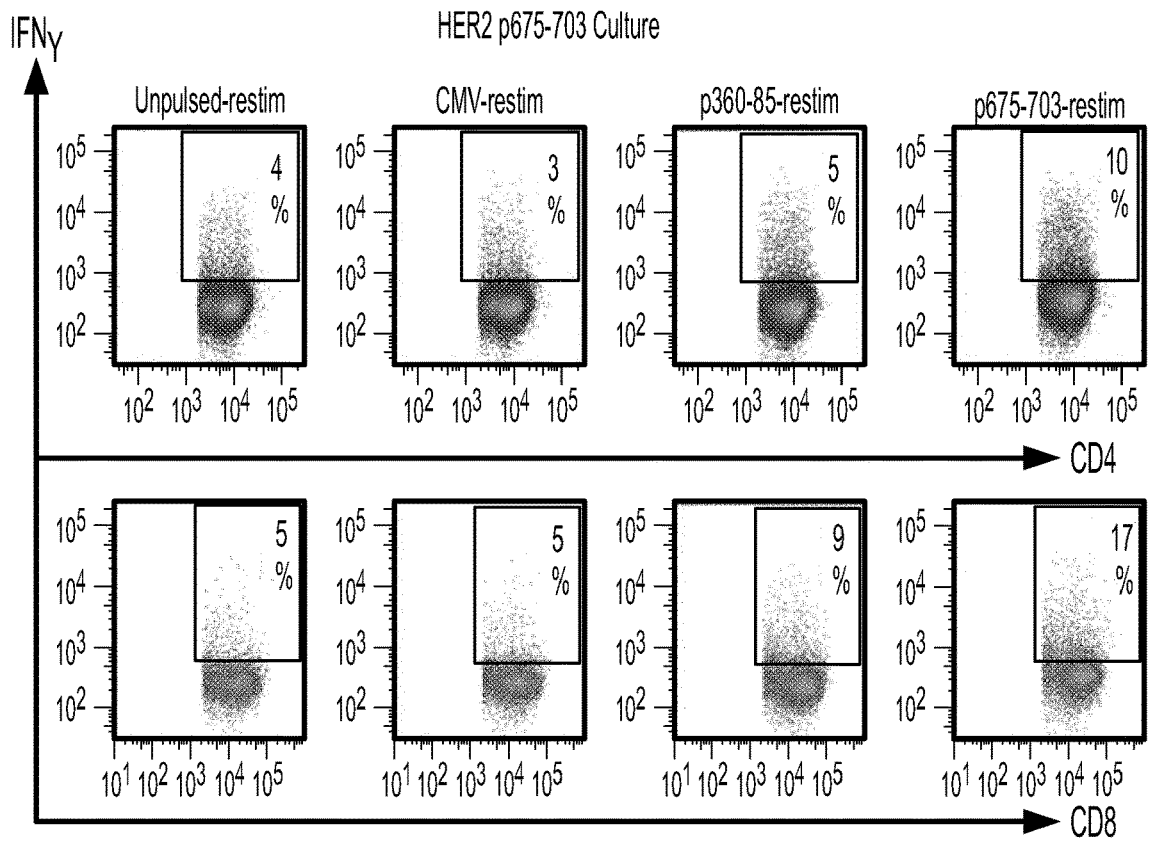
FIG. 5C is a dot plot from an intracellular cytokine assay, plotting IFNγ levels of T-cells in response to different restimulatory conditions after T-cell cultures were initially stimulated with the HER2/neu-derived p675-703 peptide sequences.
Figure 5D:
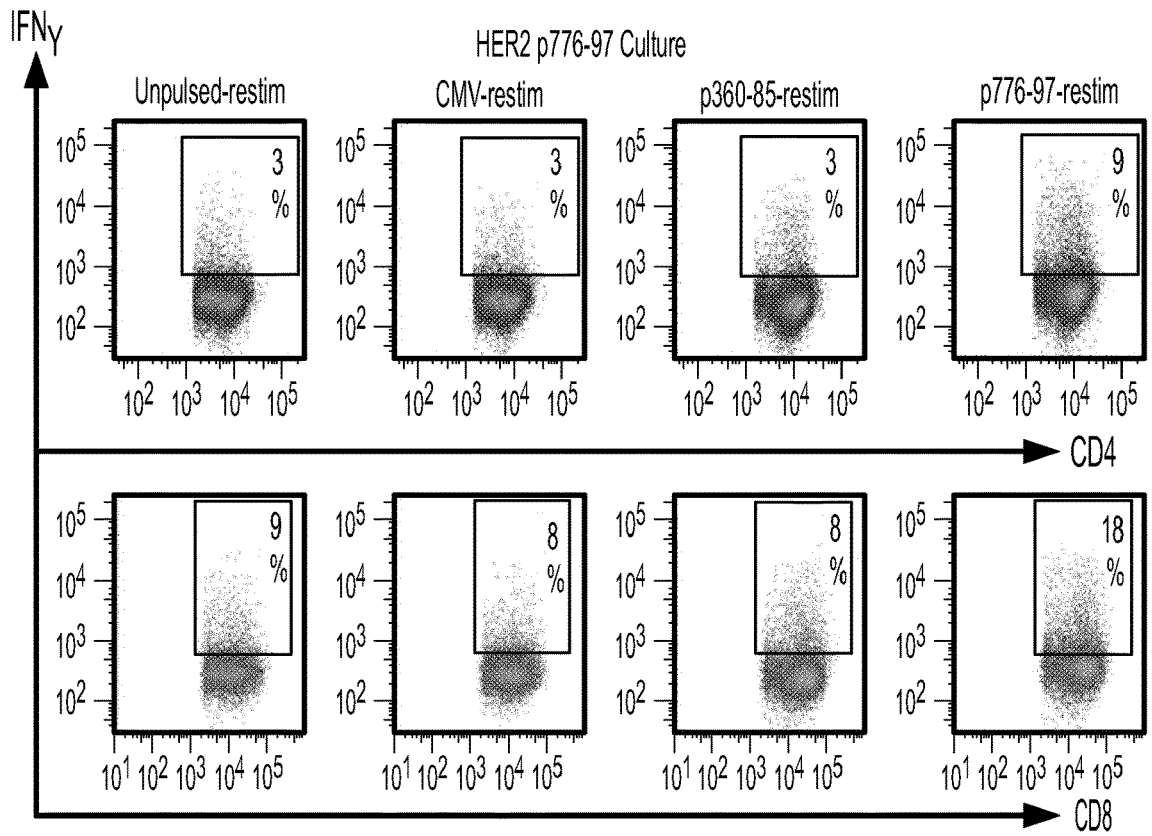
FIG. 5D is a dot plot from an intracellular cytokine assay, plotting IFNγ levels of T-cells in response to different restimulatory conditions after T-cell cultures were initially stimulated with the HER2/neu-derived p776-97 peptide sequences.

The synthesized long peptides were individually pulsed onto GM+R848+LPS conditioned PBMC cultures established from unvaccinated HLA-A2.1+ healthy volunteers, then expanded in rhIL-7 or rhIL-7+rhIL-2. Within 16 culture days, it was consistently possible to numerically expand and significantly increase the frequency of T-cells with natural specificity for MUC1, HER2, or CMV, both CD4+ and CD8+(FIGS. 4A, 4B, and 5A-5D). The SEA1 and SEA2 MUC1 sequences as well as CMVpp65 were highly immunogenic, whereas the VNTR non-glycosylated sequence was reproducibly less effective (FIGS. 4C and 4D). Proliferation of CD4+ and CD8+ T-cells was indistinguishable, with both subsets retaining their initial proportionality during expansion.

Figure 6:
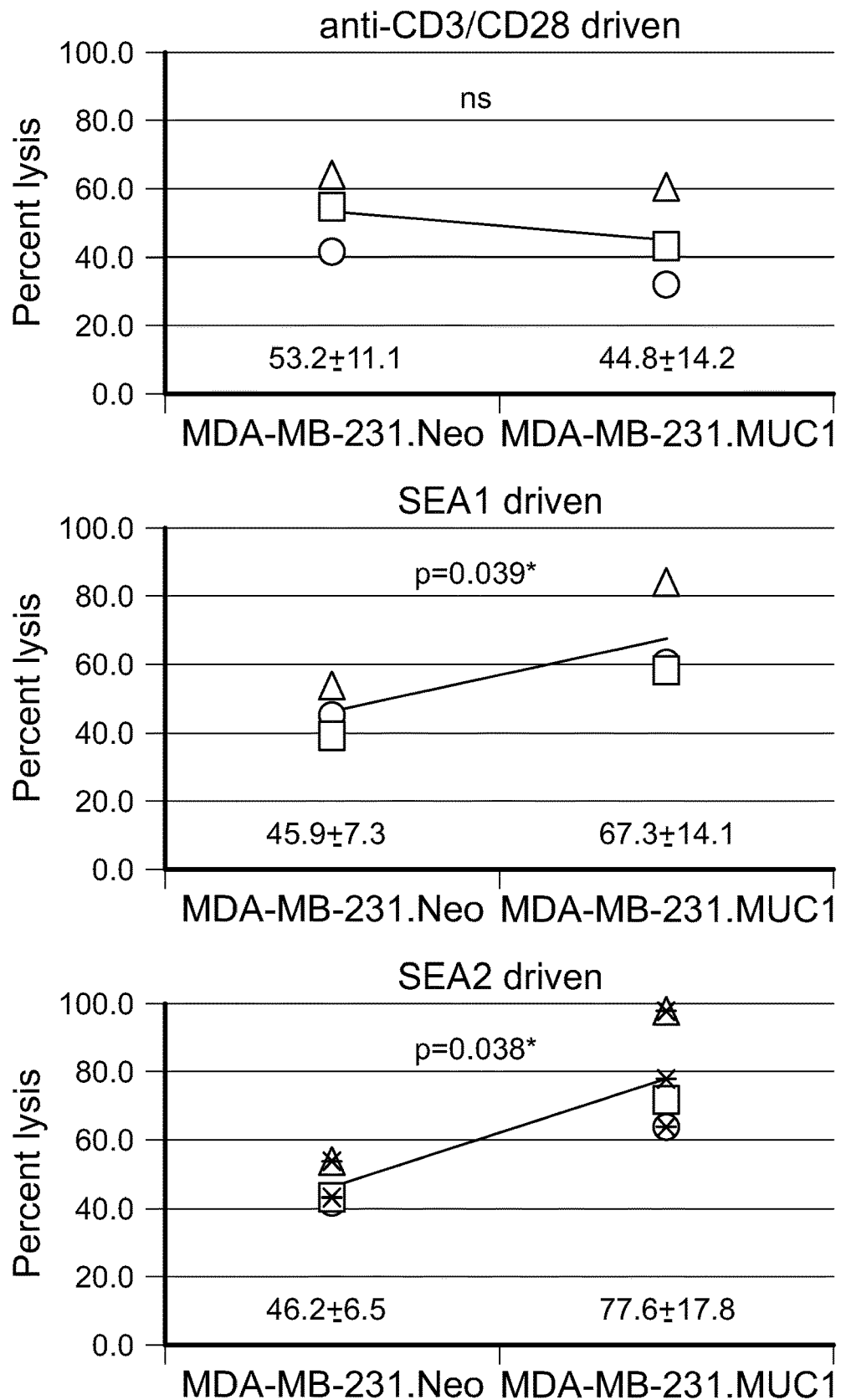
FIG. 6 is a series of graphs plotting percentage of lysis in T-cells from cultures driven polyclonally with anti-CD3/CD28 (left), driven by long peptides sequenced from the SEA1 domain of MUC1 (middle), or driven by long peptides sequenced from the SEA2 domain of MUC1 (right). At the end of T-cell culture expansion, each of the T-cell groups was transduced to express MUC1 (MDA-MB-231.MUC1) or Neo control (MDA-MB-231.Neo). SEA1- and SEA2-driven T-cells from all 3 donors (represented by triangles, circles, or squares) lysed MDA-MB-231.MUC1 targets significantly more than MDA-MB-231.Neo targets (two-tailed p=0.039 and 0.038 applying Student's paired t-test).

T-cells from GM+R848+LPS conditioned PBMC driven by either SEA2 or SEA1 long peptides not only specifically recognized one or both of these sensitizing peptides at restimulation, but also preferentially lysed the HLA-A2.1+ human breast cancer line MDA-MB-231 transduced to express MUC1 (MDA-MB-231.MUC1) compared to MDA-MB-231.Neo control targets. In contrast, polyclonally propagated PBMC T-cells (driven by anti-CD3/anti-CD28) failed to preferentially lyse MDA-MB-231.MUC1 over MDA-MB-231.Neo (FIG. 6). % Lysis was calculated as ((Experimental Lysis–Spontaneous $Cr^{51}$ release)/(Complete Lysis in Triton X-100-Spontaneous Cry' release))×100. % lysis of MDA-MB-231.Neo was statistically indistinguishable for all 3 donors whether cultures were polyclonally-, SEA1- or SEA2-driven. Polyclonally driven T-cells from all 3 donors lysed MDA-MB-231.MUC1 indistinguishably from MDA-MB-231.Neo. In contrast, SEA1- and SEA2-driven T-cells from all 3 donors lysed MDA-MB-231.MUC1 targets significantly more than MDA-MB-231.Neo targets (two-tailed p=0.039 and 0.038 applying Student's paired t-test).

Figure 7:
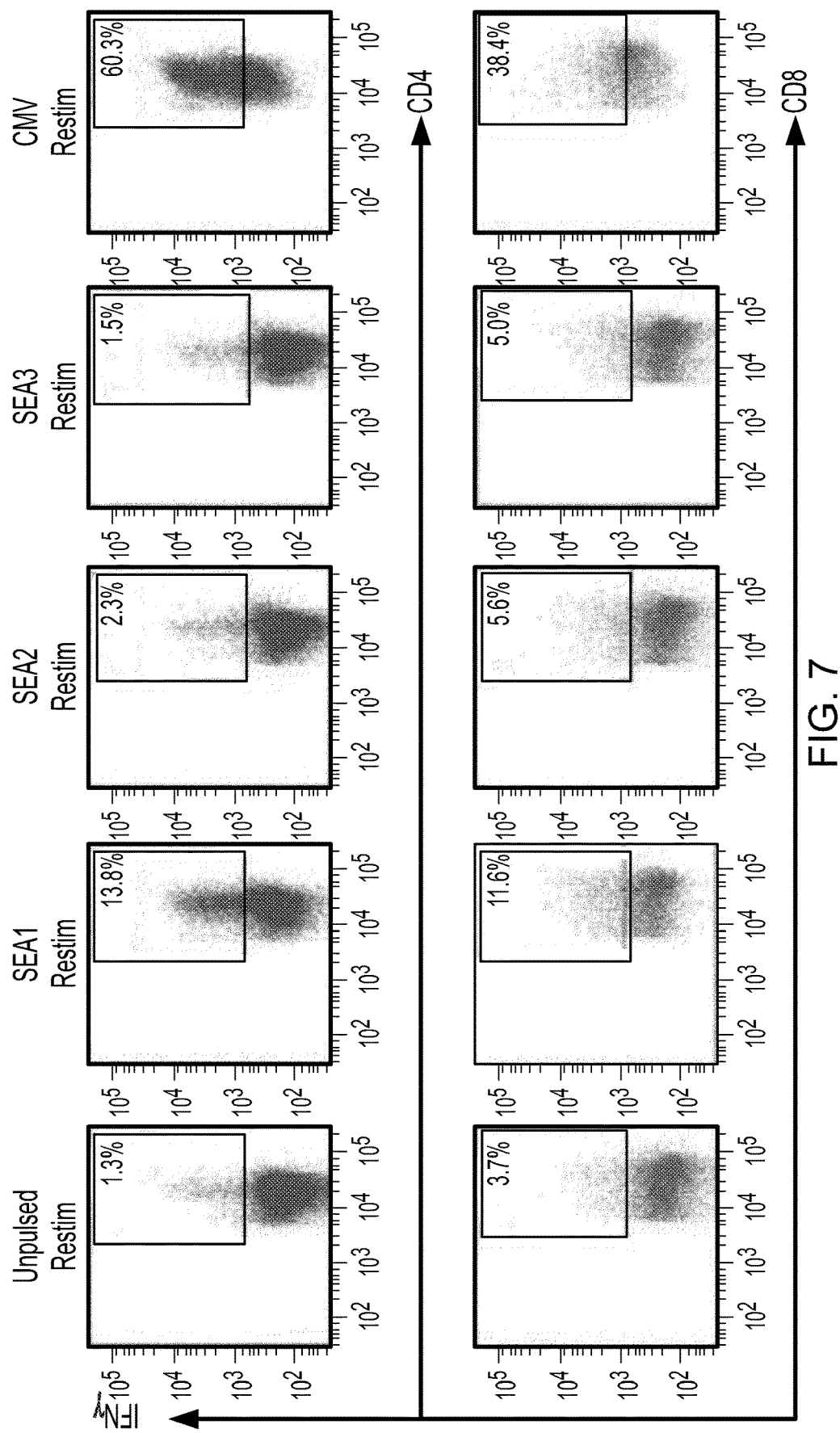
FIG. 7 is a series of dot plots from intracellular cytokine assays, plotting IFNγ levels of T-cells cultured from unfractionated PBMC from a patient with advanced breast cancer in response to different restimulatory conditions (unpulsed, or pulsed with a cocktail of SEA1, SEA2, SEA3, or CMV peptides).

Preliminary PBMC cultures established from four breast cancer patients indicated that the presently described culture system could be applied successfully to patients with malignancies (FIG. 7). Furthermore, cultures could be conducted in expansile 1 liter vessels at least as effectively as in 24 well cluster plates, and cocktails of long peptides could be employed to simultaneously expand T-cells encompassing a variety of oncoprotein specificities (FIG. 7). Furthermore, T-cells cryopreserved at the end of culture fully retained their capacity for Ag-specific IFNγ production upon subsequent re-thaw.

These results demonstrated that the cocktail sensitized and expanded the patient's T-cells to recognize each of the antigens in the cocktail.

Example 3—Preservation of T-Cell Antigen-Specific IFNγ Secretion

Whether PBMC-derived human T-cells retained their facility for secreting Ag-specific IFNγ after recryopreservation at culture's end was examined.

PBMCs cryopreserved at the time of initial collection were thawed, activated with GM-CSF, pulsed with CMVpp65 or SEA1 peptides, exposed to R848 and LPS, and then expanded to Day 19 in culture with IL-7. T-cells were harvested on Day 19, and half the cells were recryopreserved for 4 hours and re-thawed later that day. "Fresh" vs "Recryopreserved" T-cells were compared in a restimulatory intracellular IFNγ cytokine assay. Each bar shows % of CD4+ or CD8+ T-cells making IFNγ upon specific reexposure to CMVpp65 or SEA1 (subtracting background % IFNγ in the absence of Ag reexposure).

Figure 8:
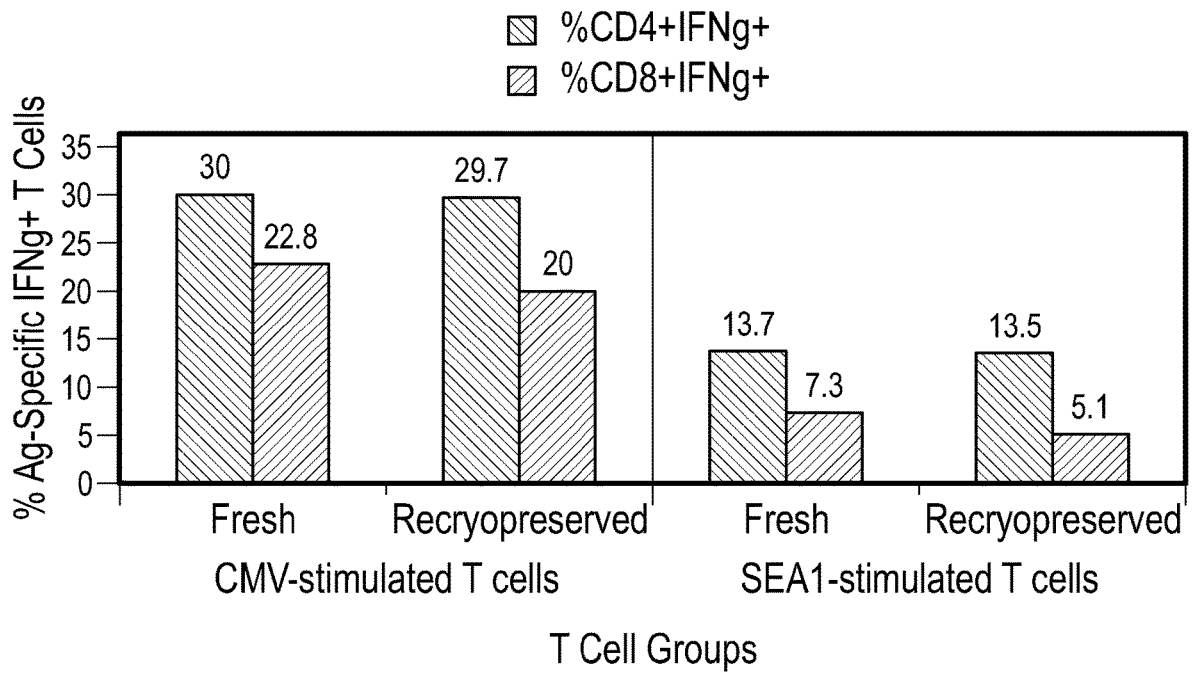
FIG. 8 is a graph plotting the percentage of antigen (Ag) specific IFNγ T cells in fresh and recryopreserved T cells stimulated with either CMVpp65 or SEA1 peptides. The percentage of $CD4^+$ and $CD8^+$ T-cells making IFNγ upon specific reexposure to CMVpp65 or SEA1 is shown. Data is representative of three biological replicates.

As shown in FIG. 8, the T-cells can be recryopreserved at the end of culture expansion and still react specifically to the sensitizing peptides after they are re-thawed. Thus, already expanded T-cells can be stored recryopreserved for future therapy.

These results demonstrated that culture-expanded T-cells can be cryopreserved for future therapeutic use without losing their ability to secrete IFNγ upon reexposure to the activating antigen.

Example 4—Modification of Long Polypeptides

The effect of post-translational modification on long polypeptides was examined.

Amidated polypeptides were amidated at the C-terminus as described elsewhere (see, e.g., Brinckerhoff et al., *Int. J. Cancer* 83(3):326-34 (1999)).

Figure 9:
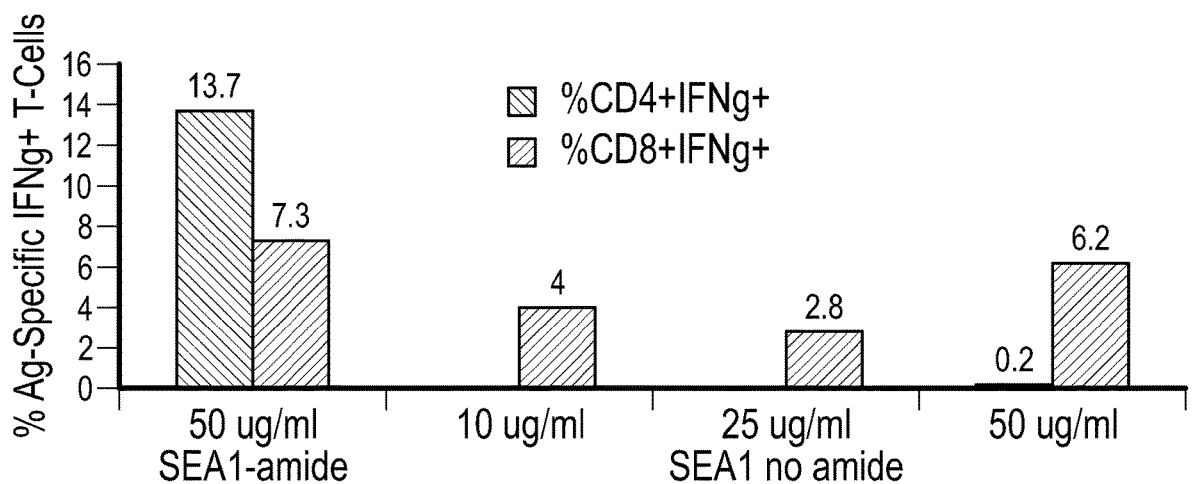
FIG. 9 is a graph plotting the percentage of Ag-specific IFNγ T cells stimulated with different concentrations of SEA1 peptides with (SEAL-amide) or without C-terminal amidation.

For the healthy donor shown in FIG. 9, amidation of the SEA1 C-terminus (SEA1-amide) rendered it far superior for sensitizing SEA1-specific CD4+IFNγ-producing T-cells when this donor's PBMC were conditioned in a standard way with GM-CSF, R848, LPS and IL-7 (FIG. 9). The SEA1-specific CD8+ T-cell response was less affected by amidation. A cocktail of peptides such as SEA1, SEA1-amide, acetyl-SEA1 and acetyl-SEA1-amide can be used to capture a broadened SEA1 response (or similarly for any other peptide).

These results demonstrated that amide modification of the C-terminus can modify the immunogenicity of an antigenic polypeptide.

Example 5—Use of Long Polypeptides Having Promiscuous MHC Binding Capabilities to Treat Cancer Patients are diagnosed with Stage III breast cancer that is MUC1 positive. Following surgery and appropriate chemotherapy and/or radiation, the patients are given a vaccine containing at least one MUC1 polypeptide described herein (e.g., SEQ ID NOs:2-7) and a TLR-agonist. Examples of TLR-agonists included, without limitation, CpG, aluminum sulfate, aluminum phosphate, MF59, Pam3CSK4, LPS, polyIC, imiquimod, and R848.

Before, during, and after vaccination, a small amount of the patients' blood optionally is harvested through venipuncture to confirm the efficacy of the vaccine. In some cases, the patients are given an anti-PD-1 antibody or an anti-PD-L1 antibody to prevent a robust immune response against the tumor cells from being inhibited. After treatment, the patients are followed for about 10 years to confirm a lack of recurrence.

If recurrence occurs (e.g., metastasis to bones and lungs), white blood cells are withdrawn via leukophoresis, and the patient's T cells are trained and grown at high numbers outside of the body to recognize one or more MUC1 polypeptides described herein. These T cells are then re-infused into the patient to treat the patient's re-occurring cancer. In some cases, the patient is given an anti-PD-1 antibody or an anti-PD-L1 antibody to prevent a robust immune response against the tumor cells from being inhibited.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising at least one isolated polypeptide, wherein the amino acid sequence of said at least one isolated polypeptide consists of the amino acid sequence set forth in any one of SEQ ID NOs:1-58, wherein (a) said polypeptide is amidated at the C-terminus or acetylated at the N-terminus, (b) said composition further comprises an adjuvant, or (c) both (a) and (b).

2. The composition of claim 1, wherein said polypeptide is amidated at the C-terminus and/or acetylated at the N-terminus.

3. The composition of claim 1, wherein said composition further comprises an adjuvant.

4. The composition of claim 1, wherein the amino acid sequence of said at least one isolated polypeptide consists of the amino acid sequence set forth in any one of SEQ ID NOs:1-52.

5. A method of treating a mammal having cancer comprising cancer cells expressing an antigen or a precancerous condition comprising precancerous cells expressing said antigen, wherein said method comprises administering to said mammal a composition comprising an adjuvant and at least one polypeptide, wherein the amino acid sequence of said polypeptide consists of the sequence set forth in any one of SEQ ID NOs:1-58, and wherein said antigen comprises said amino acid sequence.

6. The method of claim 5, wherein said mammal is a human.

7. The method of claim 5, wherein said cancer is breast cancer, pancreatic cancer, ovarian cancer, stomach cancer, lung cancer, colon cancer, multiple myeloma, leukemia, brain cancer, or melanoma cancer.

8. The method of claim 5, wherein said precancerous condition is primary myelofibrosis, essential thrombocythemia, or polycythemia vera.

9. The method of claim 5, wherein said adjuvant is CpG, aluminum sulfate, aluminum phosphate, MF59, Pam3CSK4, LPS, polyIC, imiquimod, or R848.

10. The method of claim 5, wherein said polypeptide is amidated at the C-terminus and/or acetylated at the N-terminus.

11. The method of claim 5, wherein the amino acid sequence of said polypeptide consists of the sequence as set forth in any one of SEQ ID NOs: 1-52.

12. A method of inducing an immune response against at least one polypeptide, wherein the sequence of said polypeptide consists of the sequence set forth in any one of SEQ ID NOs:1-58, wherein said method comprises administering said polypeptide to a mammal in an amount effective to induce an immune response against said polypeptide.

13. The method of claim 12, wherein said polypeptide is administered in combination with an adjuvant.

14. The method of claim 13, wherein said adjuvant is CpG, aluminum sulfate, aluminum phosphate, MF59, Pam3CSK4, LPS, polyIC, imiquimod, or R848.

15. The method of claim 12, wherein said polypeptide is amidated at the C-terminus and/or acetylated at the N-terminus.

16. The method of claim 12, wherein the sequence of said polypeptide consists of the sequence set forth in any one of SEQ ID NOs:1-52.

* * * * *

SEQUENCE LISTING

<160> NUMBER OF SEQ ID NOS: 79

<210> SEQ ID NO 1
<211> LENGTH: 28
<212> TYPE: PRT
<213> ORGANISM: Artificial Sequence
<220> FEATURE:
<223> OTHER INFORMATION: immunogenic polypeptide

<400> SEQUENCE: 1

Ser Gln Glu Pro Met Ser Ile Tyr Val Tyr Ala Leu Pro Leu Lys Met
1               5                  10                  15

Leu Asn Ile Pro Ser Ile Asn Val His His Tyr Pro
            20                  25

<210> SEQ ID NO 2
<211> LENGTH: 32
<212> TYPE: PRT
<213> ORGANISM: Artificial Sequence
<220> FEATURE:
<223> OTHER INFORMATION: immunogenic polypeptide

<400> SEQUENCE: 2

Val Pro Ser Ser Thr Glu Lys Asn Ala Val Ser Met Thr Ser Ser Val
1               5                  10                  15

Leu Ser Ser His Ser Pro Gly Ser Gly Ser Ser Thr Thr Gln Gly Gln
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: immunogenic polypeptide

<400> SEQUENCE: 3

Asn Arg Pro Ala Leu Gly Ser Thr Ala Pro Pro Val His Asn Val Thr
1               5                  10                  15

Ser Ala Ser Gly Ser Ala Ser Gly Ser Ala Ser Thr Leu Val
            20                  25                  30

<210> SEQ ID NO 4
<211> LENGTH: 37
<212> TYPE: PRT
<213> ORGANISM: Artificial Sequence
<220> FEATURE:
<223> OTHER INFORMATION: immunogenic polypeptide

<400> SEQUENCE: 4

Ser Thr Ala Pro Pro Val His Asn Val Thr Ser Ala Ser Gly Ser Ala
1               5                  10                  15

Ser Gly Ser Ala Ser Thr Leu Val His Asn Gly Thr Ser Ala Arg Ala
            20                  25                  30

Thr Thr Thr Pro Ala
        35

<210> SEQ ID NO 5
<211> LENGTH: 34
<212> TYPE: PRT
<213> ORGANISM: Artificial Sequence
<220> FEATURE:
<223> OTHER INFORMATION: immunogenic polypeptide

<400> SEQUENCE: 5

```
Ser Thr Ser Pro Gln Leu Ser Thr Gly Val Ser Phe Phe Leu Ser
1               5                   10                  15

Phe His Ile Ser Asn Leu Gln Phe Asn Ser Ser Leu Glu Asp Pro Ser
            20                  25                  30

Thr Asp

<210> SEQ ID NO 6
<211> LENGTH: 39
<212> TYPE: PRT
<213> ORGANISM: Artificial Sequence
<220> FEATURE:
<223> OTHER INFORMATION: immunogenic polypeptide

<400> SEQUENCE: 6

Ser Thr Asp Tyr Tyr Gln Glu Leu Gln Arg Asp Ile Ser Glu Met Phe
1               5                   10                  15

Leu Gln Ile Tyr Lys Gln Gly Gly Phe Leu Gly Leu Ser Asn Ile Lys
            20                  25                  30

Phe Arg Pro Gly Ser Val Val
        35

<210> SEQ ID NO 7
<211> LENGTH: 34
<212> TYPE: PRT
<213> ORGANISM: Artificial Sequence
<220> FEATURE:
<223> OTHER INFORMATION: immunogenic polypeptide

<400> SEQUENCE: 7

Val His Asp Val Glu Thr Gln Phe Asn Gln Tyr Lys Thr Glu Ala Ala
1               5                   10                  15

Ser Arg Tyr Asn Leu Thr Ile Ser Asp Val Ser Val Ser Asp Val Pro
            20                  25                  30

Phe Pro

<210> SEQ ID NO 8
<211> LENGTH: 27
<212> TYPE: PRT
<213> ORGANISM: Artificial Sequence
<220> FEATURE:
<223> OTHER INFORMATION: immunogenic polypeptide

<400> SEQUENCE: 8

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr
            20                  25

<210> SEQ ID NO 9
<211> LENGTH: 28
<212> TYPE: PRT
<213> ORGANISM: Artificial Sequence
<220> FEATURE:
<223> OTHER INFORMATION: immunogenic polypeptide

<400> SEQUENCE: 9

Pro Ala Ser Pro Glu Thr His Leu Asp Met Leu Arg His Leu Tyr Gln
1               5                   10                  15

Gly Cys Gln Val Val Gln Gly Asn Leu Glu Leu Thr
            20                  25

<210> SEQ ID NO 10
```

```
<211> LENGTH: 26
<212> TYPE: PRT
<213> ORGANISM: Artificial Sequence
<220> FEATURE:
<223> OTHER INFORMATION: immunogenic polypeptide

<400> SEQUENCE: 10

Val Val Gln Gly Asn Leu Glu Leu Thr Tyr Leu Pro Thr Asn Ala Ser
1               5                   10                  15

Leu Ser Phe Leu Gln Asp Ile Gln Glu Val
            20                  25

<210> SEQ ID NO 11
<211> LENGTH: 29
<212> TYPE: PRT
<213> ORGANISM: Artificial Sequence
<220> FEATURE:
<223> OTHER INFORMATION: immunogenic polypeptide

<400> SEQUENCE: 11

Leu Ser Phe Leu Gln Asp Ile Gln Glu Val Gln Gly Tyr Val Leu Ile
1               5                   10                  15

Ala His Asn Gln Val Arg Gln Val Pro Leu Gln Arg Leu
            20                  25

<210> SEQ ID NO 12
<211> LENGTH: 29
<212> TYPE: PRT
<213> ORGANISM: Artificial Sequence
<220> FEATURE:
<223> OTHER INFORMATION: immunogenic polypeptide

<400> SEQUENCE: 12

Ala His Asn Gln Val Arg Gln Val Pro Leu Gln Arg Leu Arg Ile Val
1               5                   10                  15

Arg Gly Thr Gln Leu Phe Glu Asp Asn Tyr Ala Leu Ala
            20                  25

<210> SEQ ID NO 13
<211> LENGTH: 29
<212> TYPE: PRT
<213> ORGANISM: Artificial Sequence
<220> FEATURE:
<223> OTHER INFORMATION: immunogenic polypeptide

<400> SEQUENCE: 13

Thr Glu Ile Leu Lys Gly Gly Val Leu Ile Gln Arg Asn Pro Gln Leu
1               5                   10                  15

Cys Tyr Gln Asp Thr Ile Leu Trp Lys Asp Ile Phe His
            20                  25

<210> SEQ ID NO 14
<211> LENGTH: 33
<212> TYPE: PRT
<213> ORGANISM: Artificial Sequence
<220> FEATURE:
<223> OTHER INFORMATION: immunogenic polypeptide

<400> SEQUENCE: 14

Tyr Gln Asp Thr Ile Leu Trp Lys Asp Ile Phe His Lys Asn Asn Gln
1               5                   10                  15

Leu Ala Leu Thr Leu Ile Asp Thr Asn Arg Ser Arg Ala Cys His Pro
            20                  25                  30

Cys
```

<210> SEQ ID NO 15
<211> LENGTH: 23
<212> TYPE: PRT
<213> ORGANISM: Artificial Sequence
<220> FEATURE:
<223> OTHER INFORMATION: immunogenic polypeptide

<400> SEQUENCE: 15

Leu Gly Met Glu His Leu Arg Glu Val Arg Ala Val Thr Ser Ala Asn
1               5                   10                  15

Ile Gln Glu Phe Ala Gly Cys
            20

<210> SEQ ID NO 16
<211> LENGTH: 26
<212> TYPE: PRT
<213> ORGANISM: Artificial Sequence
<220> FEATURE:
<223> OTHER INFORMATION: immunogenic polypeptide

<400> SEQUENCE: 16

Asn Ile Gln Glu Phe Ala Gly Cys Lys Lys Ile Phe Gly Ser Leu Ala
1               5                   10                  15

Phe Leu Pro Glu Ser Phe Asp Gly Asp Pro
            20                  25

<210> SEQ ID NO 17
<211> LENGTH: 26
<212> TYPE: PRT
<213> ORGANISM: Artificial Sequence
<220> FEATURE:
<223> OTHER INFORMATION: immunogenic polypeptide

<400> SEQUENCE: 17

Val Phe Glu Thr Leu Glu Glu Ile Thr Gly Tyr Leu Tyr Ile Ser Ala
1               5                   10                  15

Trp Pro Asp Ser Leu Pro Asp Leu Ser Val
            20                  25

<210> SEQ ID NO 18
<211> LENGTH: 29
<212> TYPE: PRT
<213> ORGANISM: Artificial Sequence
<220> FEATURE:
<223> OTHER INFORMATION: immunogenic polypeptide

<400> SEQUENCE: 18

Asp Leu Ser Val Phe Gln Asn Leu Gln Val Ile Arg Gly Arg Ile Leu
1               5                   10                  15

His Asn Gly Ala Tyr Ser Leu Thr Leu Gln Gly Leu Gly
            20                  25

<210> SEQ ID NO 19
<211> LENGTH: 28
<212> TYPE: PRT
<213> ORGANISM: Artificial Sequence
<220> FEATURE:
<223> OTHER INFORMATION: immunogenic polypeptide

<400> SEQUENCE: 19

Thr Leu Gln Gly Leu Gly Ile Ser Trp Leu Gly Leu Arg Ser Leu Arg
1               5                   10                  15

Glu Leu Gly Ser Gly Leu Ala Leu Ile His His Asn

<210> SEQ ID NO 20
<211> LENGTH: 23
<212> TYPE: PRT
<213> ORGANISM: Artificial Sequence
<220> FEATURE:
<223> OTHER INFORMATION: immunogenic polypeptide

<400> SEQUENCE: 20

Glu Leu Gly Ser Gly Leu Ala Leu Ile His His Asn Thr His Leu Cys
1               5                   10                  15

Phe Val His Thr Val Pro Trp
            20

<210> SEQ ID NO 21
<211> LENGTH: 21
<212> TYPE: PRT
<213> ORGANISM: Artificial Sequence
<220> FEATURE:
<223> OTHER INFORMATION: immunogenic polypeptide

<400> SEQUENCE: 21

His Asn Thr His Leu Cys Phe Val His Thr Val Pro Trp Asp Gln Leu
1               5                   10                  15

Phe Arg Asn Pro His
            20

<210> SEQ ID NO 22
<211> LENGTH: 21
<212> TYPE: PRT
<213> ORGANISM: Artificial Sequence
<220> FEATURE:
<223> OTHER INFORMATION: immunogenic polypeptide

<400> SEQUENCE: 22

Pro Ser Gly Val Lys Pro Asp Leu Ser Tyr Met Pro Ile Trp Lys Phe
1               5                   10                  15

Pro Asp Glu Glu Gly
            20

<210> SEQ ID NO 23
<211> LENGTH: 22
<212> TYPE: PRT
<213> ORGANISM: Artificial Sequence
<220> FEATURE:
<223> OTHER INFORMATION: immunogenic polypeptide

<400> SEQUENCE: 23

Glu Gln Arg Ala Ser Pro Leu Thr Ser Ile Ile Ser Ala Val Val Gly
1               5                   10                  15

Ile Leu Leu Val Val Val
            20

<210> SEQ ID NO 24
<211> LENGTH: 29
<212> TYPE: PRT
<213> ORGANISM: Artificial Sequence
<220> FEATURE:
<223> OTHER INFORMATION: immunogenic polypeptide

<400> SEQUENCE: 24

Ile Lys Arg Arg Gln Gln Lys Ile Arg Lys Tyr Thr Met Arg Arg Leu
1               5                   10                  15

Leu Gln Glu Thr Glu Leu Val Glu Pro Leu Thr Pro Ser
            20                  25

<210> SEQ ID NO 25
<211> LENGTH: 28
<212> TYPE: PRT
<213> ORGANISM: Artificial Sequence
<220> FEATURE:
<223> OTHER INFORMATION: immunogenic polypeptide

<400> SEQUENCE: 25

Gln Ala Gln Met Arg Ile Leu Lys Glu Thr Glu Leu Arg Lys Val Lys
1               5                   10                  15

Val Leu Gly Ser Gly Ala Phe Gly Thr Val Tyr Lys
            20                  25

<210> SEQ ID NO 26
<211> LENGTH: 26
<212> TYPE: PRT
<213> ORGANISM: Artificial Sequence
<220> FEATURE:
<223> OTHER INFORMATION: immunogenic polypeptide

<400> SEQUENCE: 26

Gly Val Gly Ser Pro Tyr Val Ser Arg Leu Leu Gly Ile Cys Leu Thr
1               5                   10                  15

Ser Thr Val Gln Leu Val Thr Gln Leu Met
            20                  25

<210> SEQ ID NO 27
<211> LENGTH: 21
<212> TYPE: PRT
<213> ORGANISM: Artificial Sequence
<220> FEATURE:
<223> OTHER INFORMATION: immunogenic polypeptide

<400> SEQUENCE: 27

Asp Leu Leu Asn Trp Cys Met Gln Ile Ala Lys Gly Met Ser Tyr Leu
1               5                   10                  15

Glu Asp Val Arg Leu
            20

<210> SEQ ID NO 28
<211> LENGTH: 21
<212> TYPE: PRT
<213> ORGANISM: Artificial Sequence
<220> FEATURE:
<223> OTHER INFORMATION: immunogenic polypeptide

<400> SEQUENCE: 28

Leu Glu Asp Val Arg Leu Val His Arg Asp Leu Ala Ala Arg Asn Val
1               5                   10                  15

Leu Val Lys Ser Pro
            20

<210> SEQ ID NO 29
<211> LENGTH: 21
<212> TYPE: PRT
<213> ORGANISM: Artificial Sequence
<220> FEATURE:
<223> OTHER INFORMATION: immunogenic polypeptide

<400> SEQUENCE: 29

Asp Leu Ala Ala Arg Asn Val Leu Val Lys Ser Pro Asn His Val Lys
1               5                   10                  15

Ile Thr Asp Phe Gly
            20

<210> SEQ ID NO 30
<211> LENGTH: 24
<212> TYPE: PRT
<213> ORGANISM: Artificial Sequence
<220> FEATURE:
<223> OTHER INFORMATION: immunogenic polypeptide

<400> SEQUENCE: 30

Asp Gly Gly Lys Val Pro Ile Lys Trp Met Ala Leu Glu Ser Ile Leu
1               5                   10                  15

Arg Arg Arg Phe Thr His Gln Ser
            20

<210> SEQ ID NO 31
<211> LENGTH: 19
<212> TYPE: PRT
<213> ORGANISM: Artificial Sequence
<220> FEATURE:
<223> OTHER INFORMATION: immunogenic polypeptide

<400> SEQUENCE: 31

Glu Ser Ile Leu Arg Arg Arg Phe Thr His Gln Ser Asp Val Trp Ser
1               5                   10                  15

Tyr Gly Val

<210> SEQ ID NO 32
<211> LENGTH: 27
<212> TYPE: PRT
<213> ORGANISM: Artificial Sequence
<220> FEATURE:
<223> OTHER INFORMATION: immunogenic polypeptide

<400> SEQUENCE: 32

Arg Leu Pro Gln Pro Pro Ile Cys Thr Ile Asp Val Tyr Met Ile Met
1               5                   10                  15

Val Lys Cys Trp Met Ile Asp Ser Glu Cys Arg
            20                  25

<210> SEQ ID NO 33
<211> LENGTH: 28
<212> TYPE: PRT
<213> ORGANISM: Artificial Sequence
<220> FEATURE:
<223> OTHER INFORMATION: immunogenic polypeptide

<400> SEQUENCE: 33

Ser Glu Cys Arg Pro Arg Phe Arg Glu Leu Val Ser Glu Phe Ser Arg
1               5                   10                  15

Met Ala Arg Asp Pro Gln Arg Phe Val Val Ile Gln
            20                  25

<210> SEQ ID NO 34
<211> LENGTH: 20
<212> TYPE: PRT
<213> ORGANISM: Artificial Sequence
<220> FEATURE:
<223> OTHER INFORMATION: immunogenic polypeptide

<400> SEQUENCE: 34

Ala Arg Asp Pro Gln Arg Phe Val Val Ile Gln Asn Glu Asp Leu Gly
1               5                   10                  15

```
Pro Ala Ser Pro
        20

<210> SEQ ID NO 35
<211> LENGTH: 27
<212> TYPE: PRT
<213> ORGANISM: Artificial Sequence
<220> FEATURE:
<223> OTHER INFORMATION: immunogenic polypeptide

<400> SEQUENCE: 35

Ala Leu Gly Ser Leu Leu Phe Leu Leu Phe Ser Leu Gly Trp Val Gln
1               5                   10                  15

Pro Ser Arg Thr Leu Ala Gly Glu Thr Gly Gln
            20                  25

<210> SEQ ID NO 36
<211> LENGTH: 27
<212> TYPE: PRT
<213> ORGANISM: Artificial Sequence
<220> FEATURE:
<223> OTHER INFORMATION: immunogenic polypeptide

<400> SEQUENCE: 36

Gly Leu Ser Thr Glu Arg Val Arg Glu Leu Ala Val Ala Leu Ala Gln
1               5                   10                  15

Lys Asn Val Lys Leu Ser Thr Glu Gln Leu Arg
            20                  25

<210> SEQ ID NO 37
<211> LENGTH: 23
<212> TYPE: PRT
<213> ORGANISM: Artificial Sequence
<220> FEATURE:
<223> OTHER INFORMATION: immunogenic polypeptide

<400> SEQUENCE: 37

Leu Asp Ala Leu Pro Leu Asp Leu Leu Phe Leu Asn Pro Asp Ala
1               5                   10                  15

Phe Ser Gly Pro Gln Ala Cys
            20

<210> SEQ ID NO 38
<211> LENGTH: 33
<212> TYPE: PRT
<213> ORGANISM: Artificial Sequence
<220> FEATURE:
<223> OTHER INFORMATION: immunogenic polypeptide

<400> SEQUENCE: 38

Phe Leu Asn Pro Asp Ala Phe Ser Gly Pro Gln Ala Cys Thr Arg Phe
1               5                   10                  15

Phe Ser Arg Ile Thr Lys Ala Asn Val Asp Leu Leu Pro Arg Gly Ala
            20                  25                  30

Pro

<210> SEQ ID NO 39
<211> LENGTH: 44
<212> TYPE: PRT
<213> ORGANISM: Artificial Sequence
<220> FEATURE:
<223> OTHER INFORMATION: immunogenic polypeptide

<400> SEQUENCE: 39
```

Pro Ser Thr Trp Ser Val Ser Thr Met Asp Ala Leu Arg Gly Leu Leu
1               5                   10                  15

Pro Val Leu Gly Gln Pro Ile Ile Arg Ser Ile Pro Gln Gly Ile Val
            20                  25                  30

Ala Ala Trp Arg Gln Arg Ser Ser Arg Asp Pro Ser
        35                  40

<210> SEQ ID NO 40
<211> LENGTH: 30
<212> TYPE: PRT
<213> ORGANISM: Artificial Sequence
<220> FEATURE:
<223> OTHER INFORMATION: immunogenic polypeptide

<400> SEQUENCE: 40

Pro Ser Thr Trp Ser Val Ser Thr Met Asp Ala Leu Arg Gly Leu Leu
1               5                   10                  15

Pro Val Leu Gly Gln Pro Ile Ile Arg Ser Ile Pro Gln Gly
            20                  25                  30

<210> SEQ ID NO 41
<211> LENGTH: 34
<212> TYPE: PRT
<213> ORGANISM: Artificial Sequence
<220> FEATURE:
<223> OTHER INFORMATION: immunogenic polypeptide

<400> SEQUENCE: 41

Ala Leu Arg Gly Leu Leu Pro Val Leu Gly Gln Pro Ile Ile Arg Ser
1               5                   10                  15

Ile Pro Gln Gly Ile Val Ala Ala Trp Arg Gln Arg Ser Ser Arg Asp
            20                  25                  30

Pro Ser

<210> SEQ ID NO 42
<211> LENGTH: 44
<212> TYPE: PRT
<213> ORGANISM: Artificial Sequence
<220> FEATURE:
<223> OTHER INFORMATION: immunogenic polypeptide

<400> SEQUENCE: 42

Pro Ser Thr Trp Ser Val Ser Thr Met Asp Ala Leu Arg Gly Leu Leu
1               5                   10                  15

Pro Val Leu Gly Gln Pro Ile Ile Arg Ser Ile Pro Gln Gly Ile Val
            20                  25                  30

Ala Ala Trp Arg Gln Arg Ser Ser Arg Asp Pro Ser
        35                  40

<210> SEQ ID NO 43
<211> LENGTH: 29
<212> TYPE: PRT
<213> ORGANISM: Artificial Sequence
<220> FEATURE:
<223> OTHER INFORMATION: immunogenic polypeptide

<400> SEQUENCE: 43

Gln Gly Tyr Pro Glu Ser Val Ile Gln His Leu Gly Tyr Leu Phe Leu
1               5                   10                  15

Lys Met Ser Pro Glu Asp Ile Arg Lys Trp Asn Val Thr
            20                  25

```
<210> SEQ ID NO 44
<211> LENGTH: 25
<212> TYPE: PRT
<213> ORGANISM: Artificial Sequence
<220> FEATURE:
<223> OTHER INFORMATION: immunogenic polypeptide

<400> SEQUENCE: 44

Pro Glu Asp Ile Arg Lys Trp Asn Val Thr Ser Leu Glu Thr Leu Lys
1               5                   10                  15

Ala Leu Leu Glu Val Asn Lys Gly His
            20                  25

<210> SEQ ID NO 45
<211> LENGTH: 22
<212> TYPE: PRT
<213> ORGANISM: Artificial Sequence
<220> FEATURE:
<223> OTHER INFORMATION: immunogenic polypeptide

<400> SEQUENCE: 45

Asn Met Asn Gly Ser Glu Tyr Phe Val Lys Ile Gln Ser Phe Leu Gly
1               5                   10                  15

Gly Ala Pro Thr Glu Asp
            20

<210> SEQ ID NO 46
<211> LENGTH: 28
<212> TYPE: PRT
<213> ORGANISM: Artificial Sequence
<220> FEATURE:
<223> OTHER INFORMATION: immunogenic polypeptide

<400> SEQUENCE: 46

Ser Gln Gln Asn Val Ser Met Asp Leu Ala Thr Phe Met Lys Leu Arg
1               5                   10                  15

Thr Asp Ala Val Leu Pro Leu Thr Val Ala Glu Val
            20                  25

<210> SEQ ID NO 47
<211> LENGTH: 27
<212> TYPE: PRT
<213> ORGANISM: Artificial Sequence
<220> FEATURE:
<223> OTHER INFORMATION: immunogenic polypeptide

<400> SEQUENCE: 47

Ser Gln Gln Asn Val Ser Met Asp Leu Ala Thr Phe Met Lys Leu Arg
1               5                   10                  15

Thr Asp Ala Val Leu Pro Leu Thr Val Ala Glu
            20                  25

<210> SEQ ID NO 48
<211> LENGTH: 25
<212> TYPE: PRT
<213> ORGANISM: Artificial Sequence
<220> FEATURE:
<223> OTHER INFORMATION: immunogenic polypeptide

<400> SEQUENCE: 48

Asp Ala Val Leu Pro Leu Thr Val Ala Glu Val Gln Lys Leu Leu Gly
1               5                   10                  15

Pro His Val Glu Gly Leu Lys Ala Glu
            20                  25
```

<210> SEQ ID NO 49
<211> LENGTH: 30
<212> TYPE: PRT
<213> ORGANISM: Artificial Sequence
<220> FEATURE:
<223> OTHER INFORMATION: immunogenic polypeptide

<400> SEQUENCE: 49

Gly Gly Ile Pro Asn Gly Tyr Leu Val Leu Asp Leu Ser Met Gln Glu
1               5                   10                  15

Ala Leu Ser Gly Thr Pro Cys Leu Leu Gly Pro Gly Pro Val
            20                  25                  30

<210> SEQ ID NO 50
<211> LENGTH: 21
<212> TYPE: PRT
<213> ORGANISM: Artificial Sequence
<220> FEATURE:
<223> OTHER INFORMATION: immunogenic polypeptide

<400> SEQUENCE: 50

Met Trp Met Gly Leu Ile Gln Leu Val Glu Gly Val Lys Arg Lys Asp
1               5                   10                  15

Gln Gly Phe Leu Glu
            20

<210> SEQ ID NO 51
<211> LENGTH: 32
<212> TYPE: PRT
<213> ORGANISM: Artificial Sequence
<220> FEATURE:
<223> OTHER INFORMATION: immunogenic polypeptide

<400> SEQUENCE: 51

Gly Phe Leu Glu Lys Glu Phe Tyr His Lys Thr Asn Ile Lys Met Arg
1               5                   10                  15

Cys Glu Phe Leu Ala Cys Trp Pro Ala Phe Thr Val Leu Gly Glu Ala
            20                  25                  30

<210> SEQ ID NO 52
<211> LENGTH: 29
<212> TYPE: PRT
<213> ORGANISM: Artificial Sequence
<220> FEATURE:
<223> OTHER INFORMATION: immunogenic polypeptide

<400> SEQUENCE: 52

Asp Gln Val Asp Trp Ser Arg Leu Leu Arg Asp Ala Gly Leu Val Lys
1               5                   10                  15

Met Ser Arg Lys Pro Arg Ala Ser Ser Pro Leu Ser Asn
            20                  25

<210> SEQ ID NO 53
<211> LENGTH: 40
<212> TYPE: PRT
<213> ORGANISM: Artificial Sequence
<220> FEATURE:
<223> OTHER INFORMATION: immunogenic polypeptide

<400> SEQUENCE: 53

Arg Arg Met Met Arg Thr Lys Met Arg Met Arg Met Arg Thr
1               5                   10                  15

Arg Arg Lys Met Ser Pro Ala Arg Pro Arg Thr Ser Cys Arg Glu Ala

```
              20                  25                  30

Cys Leu Gln Gly Trp Thr Glu Ala
        35                  40

<210> SEQ ID NO 54
<211> LENGTH: 24
<212> TYPE: PRT
<213> ORGANISM: Artificial Sequence
<220> FEATURE:
<223> OTHER INFORMATION: immunogenic polypeptide

<400> SEQUENCE: 54

Arg Arg Met Met Arg Thr Lys Met Arg Met Arg Met Arg Arg Thr
1               5                  10                  15

Arg Arg Lys Met Ser Pro Ala Arg
            20

<210> SEQ ID NO 55
<211> LENGTH: 18
<212> TYPE: PRT
<213> ORGANISM: Artificial Sequence
<220> FEATURE:
<223> OTHER INFORMATION: immunogenic polypeptide

<400> SEQUENCE: 55

Arg Arg Met Met Arg Thr Lys Met Arg Met Arg Met Arg Arg Thr
1               5                  10                  15

Arg Arg

<210> SEQ ID NO 56
<211> LENGTH: 32
<212> TYPE: PRT
<213> ORGANISM: Artificial Sequence
<220> FEATURE:
<223> OTHER INFORMATION: immunogenic polypeptide

<400> SEQUENCE: 56

Ser Pro Gln Leu Ser Thr Gly Val Ser Phe Phe Leu Ser Phe His
1               5                  10                  15

Ile Ser Asn Leu Gln Phe Asn Ser Ser Leu Glu Asp Pro Ser Thr Asp
            20                  25                  30

<210> SEQ ID NO 57
<211> LENGTH: 22
<212> TYPE: PRT
<213> ORGANISM: Artificial Sequence
<220> FEATURE:
<223> OTHER INFORMATION: immunogenic polypeptide

<400> SEQUENCE: 57

Gly Val Gly Ser Pro Tyr Val Ser Arg Leu Leu Gly Ile Cys Leu Thr
1               5                  10                  15

Ser Thr Val Gln Leu Val
            20

<210> SEQ ID NO 58
<211> LENGTH: 24
<212> TYPE: PRT
<213> ORGANISM: Artificial Sequence
<220> FEATURE:
<223> OTHER INFORMATION: immunogenic polypeptide

<400> SEQUENCE: 58

Ala His Gly Val Thr Ser Ala Pro Asp Thr Arg Pro Ala Pro Gly Ser
```

```
1               5                   10                  15
```
Thr Ala Pro Pro Ala His Gly Val
            20

<210> SEQ ID NO 59
<211> LENGTH: 15
<212> TYPE: PRT
<213> ORGANISM: Artificial Sequence
<220> FEATURE:
<223> OTHER INFORMATION: SEA2 epitope

<400> SEQUENCE: 59

```
Asp Tyr Tyr Gln Glu Leu Gln Arg Asp Ile Ser Glu Met Phe Leu
1               5                   10                  15
```

<210> SEQ ID NO 60
<211> LENGTH: 15
<212> TYPE: PRT
<213> ORGANISM: Artificial Sequence
<220> FEATURE:
<223> OTHER INFORMATION: SEA2 epitope

<400> SEQUENCE: 60

```
Tyr Tyr Gln Glu Leu Gln Arg Asp Ile Ser Glu Met Phe Leu Gln
1               5                   10                  15
```

<210> SEQ ID NO 61
<211> LENGTH: 15
<212> TYPE: PRT
<213> ORGANISM: Artificial Sequence
<220> FEATURE:
<223> OTHER INFORMATION: SEA2 epitope

<400> SEQUENCE: 61

```
Tyr Gln Glu Leu Gln Arg Asp Ile Ser Glu Met Phe Leu Gln Ile
1               5                   10                  15
```

<210> SEQ ID NO 62
<211> LENGTH: 15
<212> TYPE: PRT
<213> ORGANISM: Artificial Sequence
<220> FEATURE:
<223> OTHER INFORMATION: SEA2 epitope

<400> SEQUENCE: 62

```
Asp Ile Ser Glu Met Phe Leu Gln Ile Tyr Lys Gln Gly Gly Phe
1               5                   10                  15
```

<210> SEQ ID NO 63
<211> LENGTH: 15
<212> TYPE: PRT
<213> ORGANISM: Artificial Sequence
<220> FEATURE:
<223> OTHER INFORMATION: SEA2 epitope

<400> SEQUENCE: 63

```
Ile Ser Glu Met Phe Leu Gln Ile Tyr Lys Gln Gly Gly Phe Leu
1               5                   10                  15
```

<210> SEQ ID NO 64
<211> LENGTH: 15
<212> TYPE: PRT
<213> ORGANISM: Artificial Sequence
<220> FEATURE:
<223> OTHER INFORMATION: SEA2 epitope

<400> SEQUENCE: 64

```
Ser Glu Met Phe Leu Gln Ile Tyr Lys Gln Gly Gly Phe Leu Gly
1               5                   10                  15
```

<210> SEQ ID NO 65
<211> LENGTH: 15
<212> TYPE: PRT
<213> ORGANISM: Artificial Sequence
<220> FEATURE:
<223> OTHER INFORMATION: SEA2 epitope

<400> SEQUENCE: 65

```
Glu Met Phe Leu Gln Ile Tyr Lys Gln Gly Gly Phe Leu Gly Leu
1               5                   10                  15
```

<210> SEQ ID NO 66
<211> LENGTH: 15
<212> TYPE: PRT
<213> ORGANISM: Artificial Sequence
<220> FEATURE:
<223> OTHER INFORMATION: SEA2 epitope

<400> SEQUENCE: 66

```
Met Phe Leu Gln Ile Tyr Lys Gln Gly Gly Phe Leu Gly Leu Ser
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: SEA2 epitope

<400> SEQUENCE: 67

```
Phe Leu Gln Ile Tyr Lys Gln Gly Gly Phe Leu Gly Leu Ser Asn
1               5                   10                  15
```

<210> SEQ ID NO 68
<211> LENGTH: 15
<212> TYPE: PRT
<213> ORGANISM: Artificial Sequence
<220> FEATURE:
<223> OTHER INFORMATION: SEA2 epitope

<400> SEQUENCE: 68

```
Leu Gln Ile Tyr Lys Gln Gly Gly Phe Leu Gly Leu Ser Asn Ile
1               5                   10                  15
```

<210> SEQ ID NO 69
<211> LENGTH: 15
<212> TYPE: PRT
<213> ORGANISM: Artificial Sequence
<220> FEATURE:
<223> OTHER INFORMATION: SEA2 epitope

<400> SEQUENCE: 69

```
Gln Ile Tyr Lys Gln Gly Gly Phe Leu Gly Leu Ser Asn Ile Lys
1               5                   10                  15
```

<210> SEQ ID NO 70
<211> LENGTH: 15
<212> TYPE: PRT
<213> ORGANISM: Artificial Sequence
<220> FEATURE:
<223> OTHER INFORMATION: SEA2 epitope

<400> SEQUENCE: 70

```
Ile Tyr Lys Gln Gly Gly Phe Leu Gly Leu Ser Asn Ile Lys Phe
1               5                   10                  15
```

<210> SEQ ID NO 71
<211> LENGTH: 15
<212> TYPE: PRT
<213> ORGANISM: Artificial Sequence
<220> FEATURE:
<223> OTHER INFORMATION: SEA2 epitop

<400> SEQUENCE: 71

```
Tyr Lys Gln Gly Gly Phe Leu Gly Leu Ser Asn Ile Lys Phe Arg
1               5                   10                  15
```

<210> SEQ ID NO 72
<211> LENGTH: 15
<212> TYPE: PRT
<213> ORGANISM: Artificial Sequence
<220> FEATURE:
<223> OTHER INFORMATION: SEA2 epitope

<400> SEQUENCE: 72

```
Lys Gln Gly Gly Phe Leu Gly Leu Ser Asn Ile Lys Phe Arg Pro
1               5                   10                  15
```

<210> SEQ ID NO 73
<211> LENGTH: 15
<212> TYPE: PRT
<213> ORGANISM: Artificial Sequence
<220> FEATURE:
<223> OTHER INFORMATION: SEA2 epitope

<400> SEQUENCE: 73

```
Gln Gly Gly Phe Leu Gly Leu Ser Asn Ile Lys Phe Arg Pro Gly
1               5                   10                  15
```

<210> SEQ ID NO 74
<211> LENGTH: 15
<212> TYPE: PRT
<213> ORGANISM: Artificial Sequence
<220> FEATURE:
<223> OTHER INFORMATION: SEA2 epitope

<400> SEQUENCE: 74

```
Gly Phe Leu Gly Leu Ser Asn Ile Lys Phe Arg Pro Gly Ser Val
1               5                   10                  15
```

<210> SEQ ID NO 75
<211> LENGTH: 15
<212> TYPE: PRT
<213> ORGANISM: Artificial Sequence
<220> FEATURE:
<223> OTHER INFORMATION: SEA2 epitope

<400> SEQUENCE: 75

```
Phe Leu Gly Leu Ser Asn Ile Lys Phe Arg Pro Gly Ser Val Val
1               5                   10                  15
```

<210> SEQ ID NO 76
<211> LENGTH: 655
<212> TYPE: PRT
<213> ORGANISM: Homo sapiens

<400> SEQUENCE: 76

```
Met Thr Pro Gly Thr Gln Ser Pro Phe Phe Leu Leu Leu Leu Thr
1               5                   10                  15
```

```
Val Leu Thr Val Val Thr Gly Ser Gly His Ala Ser Ser Thr Pro Gly
             20                  25                  30

Gly Glu Lys Glu Thr Ser Ala Thr Gln Arg Ser Ser Val Pro Ser Ser
         35                  40                  45

Thr Glu Lys Asn Ala Val Ser Met Thr Ser Ser Val Leu Ser Ser His
     50                  55                  60

Ser Pro Gly Ser Gly Ser Ser Thr Thr Gln Gly Gln Asp Val Thr Leu
 65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
            130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Asn Arg Pro Ala Leu Gly Ser Thr Ala
            340                 345                 350

Pro Pro Val His Asn Val Thr Ser Ala Ser Gly Ser Ala Ser Gly Ser
            355                 360                 365

Ala Ser Thr Leu Val His Asn Gly Thr Ser Ala Arg Ala Thr Thr Thr
        370                 375                 380

Pro Ala Ser Lys Ser Thr Pro Phe Ser Ile Pro Ser His His Ser Asp
385                 390                 395                 400

Thr Pro Thr Thr Leu Ala Ser His Ser Thr Lys Thr Asp Ala Ser Ser
                405                 410                 415

Thr His His Ser Ser Val Pro Pro Leu Thr Ser Ser Asn His Ser Thr
            420                 425                 430

Ser Pro Gln Leu Ser Thr Gly Val Ser Phe Phe Phe Leu Ser Phe His
```

```
                435                 440                 445
Ile Ser Asn Leu Gln Phe Asn Ser Ser Leu Glu Asp Pro Ser Thr Asp
    450                 455                 460

Tyr Tyr Gln Glu Leu Gln Arg Asp Ile Ser Glu Met Phe Leu Gln Ile
465                 470                 475                 480

Tyr Lys Gln Gly Gly Phe Leu Gly Leu Ser Asn Ile Lys Phe Arg Pro
                485                 490                 495

Gly Ser Val Val Val Gln Leu Thr Leu Ala Phe Arg Glu Gly Thr Ile
            500                 505                 510

Asn Val His Asp Val Glu Thr Gln Phe Asn Gln Tyr Lys Thr Glu Ala
        515                 520                 525

Ala Ser Arg Tyr Asn Leu Thr Ile Ser Asp Val Ser Val Ser Asp Val
    530                 535                 540

Pro Phe Pro Phe Ser Ala Gln Ser Gly Ala Gly Val Pro Gly Trp Gly
545                 550                 555                 560

Ile Ala Leu Leu Val Leu Val Cys Val Leu Val Ala Leu Ala Ile Val
                565                 570                 575

Tyr Leu Ile Ala Leu Ala Val Cys Gln Cys Arg Arg Lys Asn Tyr Gly
            580                 585                 590

Gln Leu Asp Ile Phe Pro Ala Arg Asp Thr Tyr His Pro Met Ser Glu
        595                 600                 605

Tyr Pro Thr Tyr His Thr His Gly Arg Tyr Val Pro Pro Ser Ser Thr
    610                 615                 620

Asp Arg Asp Pro Tyr Glu Lys Val Ser Ala Gly Asn Gly Gly Ser Ser
625                 630                 635                 640

Leu Ser Tyr Thr Asn Pro Ala Val Ala Ala Ser Ala Asn Leu
                645                 650                 655

<210> SEQ ID NO 77
<211> LENGTH: 475
<212> TYPE: PRT
<213> ORGANISM: Homo sapiens

<400> SEQUENCE: 77

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
        130                 135                 140

Arg Pro Ala Pro Gly Ser Thr Ala Pro Pro Ala His Gly Val Thr Ser
145                 150                 155                 160
```

Ala Pro Asp Asn Arg Pro Ala Leu Gly Ser Thr Ala Pro Pro Val His
            165                 170                 175

Asn Val Thr Ser Ala Ser Gly Ser Ala Ser Gly Ser Ala Ser Thr Leu
        180                 185                 190

Val His Asn Gly Thr Ser Ala Arg Ala Thr Thr Thr Pro Ala Ser Lys
    195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240

Ser Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
    290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
    370                 375                 380

Val Leu Val Cys Val Leu Val Ala Leu Ala Ile Val Tyr Leu Ile Ala
385                 390                 395                 400

Leu Ala Val Cys Gln Cys Arg Arg Lys Asn Tyr Gly Gln Leu Asp Ile
                405                 410                 415

Phe Pro Ala Arg Asp Thr Tyr His Pro Met Ser Glu Tyr Pro Thr Tyr
            420                 425                 430

His Thr His Gly Arg Tyr Val Pro Pro Ser Ser Thr Asp Arg Ser Pro
        435                 440                 445

Tyr Glu Lys Val Ser Ala Gly Asn Gly Gly Ser Ser Leu Ser Tyr Thr
    450                 455                 460

Asn Pro Ala Val Ala Ala Thr Ser Ala Asn Leu
465                 470                 475

<210> SEQ ID NO 78
<211> LENGTH: 1255
<212> TYPE: PRT
<213> ORGANISM: Homo sapiens

<400> SEQUENCE: 78

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

-continued

```
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480
```

-continued

Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
        835                 840                 845
Arg Asn Val Leu Val Lys Ser Pro Asn His Val Lys Ile Thr Asp Phe
    850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val

```
                    900                 905                 910
Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

Ser Gly Gly Gly Asp Leu Thr Leu Gly Leu Glu Pro Ser Glu Glu
        1055                1060                1065

Glu Ala Pro Arg Ser Pro Leu Ala Pro Ser Glu Gly Ala Gly Ser
        1070                1075                1080

Asp Val Phe Asp Gly Asp Leu Gly Met Gly Ala Ala Lys Gly Leu
        1085                1090                1095

Gln Ser Leu Pro Thr His Asp Pro Ser Pro Leu Gln Arg Tyr Ser
        1100                1105                1110

Glu Asp Pro Thr Val Pro Leu Pro Ser Glu Thr Asp Gly Tyr Val
        1115                1120                1125

Ala Pro Leu Thr Cys Ser Pro Gln Pro Glu Tyr Val Asn Gln Pro
        1130                1135                1140

Asp Val Arg Pro Gln Pro Pro Ser Pro Arg Glu Gly Pro Leu Pro
        1145                1150                1155

Ala Ala Arg Pro Ala Gly Ala Thr Leu Glu Arg Pro Lys Thr Leu
        1160                1165                1170

Ser Pro Gly Lys Asn Gly Val Val Lys Asp Val Phe Ala Phe Gly
        1175                1180                1185

Gly Ala Val Glu Asn Pro Glu Tyr Leu Thr Pro Gln Gly Gly Ala
        1190                1195                1200

Ala Pro Gln Pro His Pro Pro Ala Phe Ser Pro Ala Phe Asp
        1205                1210                1215

Asn Leu Tyr Tyr Trp Asp Gln Asp Pro Pro Glu Arg Gly Ala Pro
        1220                1225                1230

Pro Ser Thr Phe Lys Gly Thr Pro Thr Ala Glu Asn Pro Glu Tyr
        1235                1240                1245

Leu Gly Leu Asp Val Pro Val
        1250                1255

<210> SEQ ID NO 79
<211> LENGTH: 40
<212> TYPE: PRT
<213> ORGANISM: Homo sapiens

<400> SEQUENCE: 79
```

-continued

```
Arg Arg Met Met Arg Thr Lys Met Arg Met Arg Arg Met Arg Arg Thr
1               5                   10                  15

Arg Arg Lys Met Ser Pro Ala Arg Pro Arg Thr Ser Cys Arg Glu Ala
            20              25                  30

Cys Leu Gln Gly Trp Thr Glu Ala
        35              40
```